(12) United States Patent
Seibel et al.

(10) Patent No.: US 6,563,105 B2
(45) Date of Patent: May 13, 2003

(54) IMAGE ACQUISITION WITH DEPTH ENHANCEMENT

(75) Inventors: Eric J. Seibel, Seattle, WA (US); Quinn Y. J. Smithwick, Bothell, WA (US); Thomas A. Furness, III, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/938,467

(22) Filed: Aug. 23, 2001

(65) Prior Publication Data

US 2002/0139920 A1 Oct. 3, 2002

Related U.S. Application Data

(63) Continuation-in-part of application No. 09/425,528, filed on Oct. 22, 1999, now Pat. No. 6,294,775.
(60) Provisional application No. 60/138,404, filed on Jun. 8, 1999.

(51) Int. Cl.[7] .............................................. H01L 27/00
(52) U.S. Cl. ................................... 250/208.1; 250/234
(58) Field of Search ........................... 250/208.1, 234, 250/235, 306, 307, 227.11, 214 VT; 359/205, 207, 213, 199, 202; 378/4, 12, 21, 36; 382/203, 204, 260

(56) References Cited

U.S. PATENT DOCUMENTS

| | | |
|---|---|---|
| 3,547,520 A | 12/1970 | Lee et al. |
| 4,264,208 A * | 4/1981 | Haberl et al. ............... 356/609 |
| 5,103,497 A | 4/1992 | Hicks |
| 5,280,377 A | 1/1994 | Chandler et al. |
| 5,557,444 A | 9/1996 | Melville et al. |
| 5,694,237 A | 12/1997 | Melville |
| 5,982,528 A | 11/1999 | Melville |

OTHER PUBLICATIONS

Horn, "Robot Vision," MIT 1986, pp. 226–232, 262–267, 276, 370–375, 388 Month unknown.
Klette, Schuns and Koschan, "Computer Vision: three Dimensional data from Images," Springer 1988 pp. 335–338. Month unknown.
Kitoh et al., "Compensation of Color Shift Due to the Multiple Reflection of Illumination in CCD . . . ," Optics Communications 143 (1997) pp. 102–108. Month unknown.
Satava, 3D Vision Technology Applied to Advanced Minimally Invasive Surgery Systems, Surgical Endoscopy (1993) 7:429–431. Month unknown.
Amann et al., "Laser Ranging: A Critical Review of Usual Techniques for Distance Measurement," Optical Engineering vol. 40 No. 1; Jan. 2001.
Bosch et al., "Optical Feedback Interferometry for Sensing Application," Optical Engineering vol. 40 No. 1 pp. 20–27 Jan. 2001.

* cited by examiner

*Primary Examiner*—Que T. Le
(74) *Attorney, Agent, or Firm*—Steven P. Koda

(57) ABSTRACT

A minimally invasive, medical, image acquisition system outputs a light beam or pulse which illuminates a precise spot size. A plurality of photon detector detect returning photons from the object, including the spot. Pixel resolution is determined by the area of the illumination spot (and thus the lens configuration), rather than an area sensed by the detector. Depth enhancement is determined by correlating images detected by the respective detectors, or alternatively by a range finding method based on phase difference, time of flight, frequency or interferometry.

35 Claims, 10 Drawing Sheets

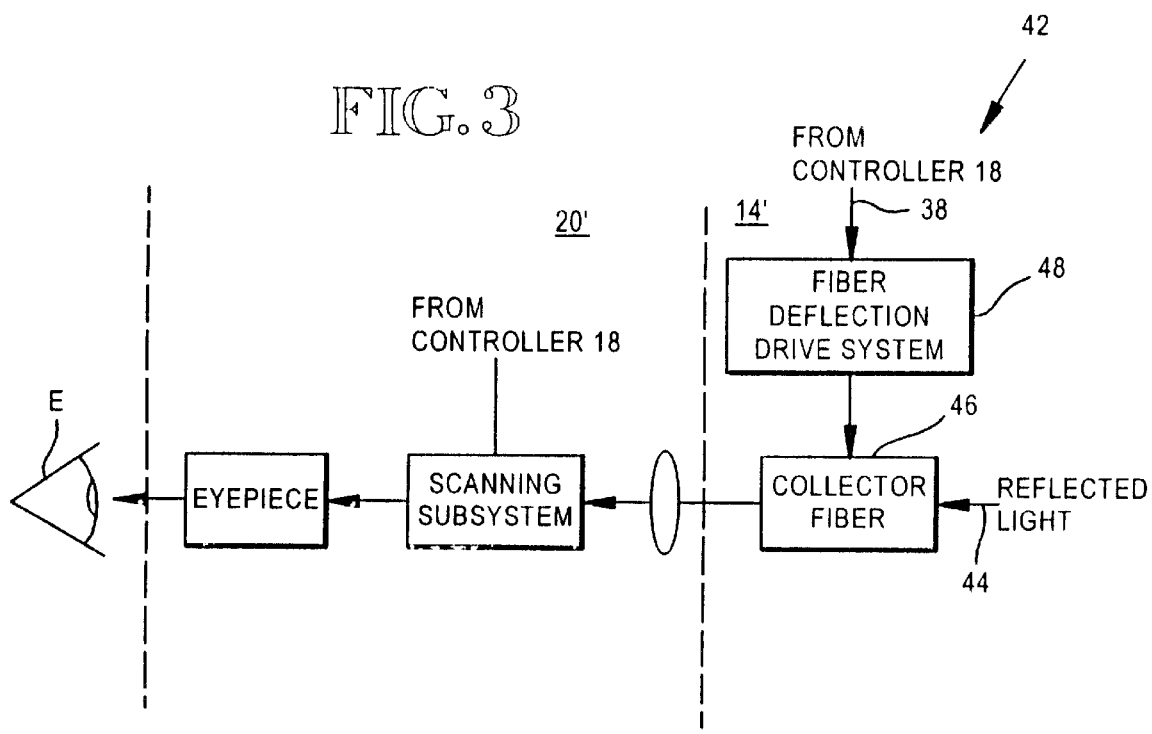
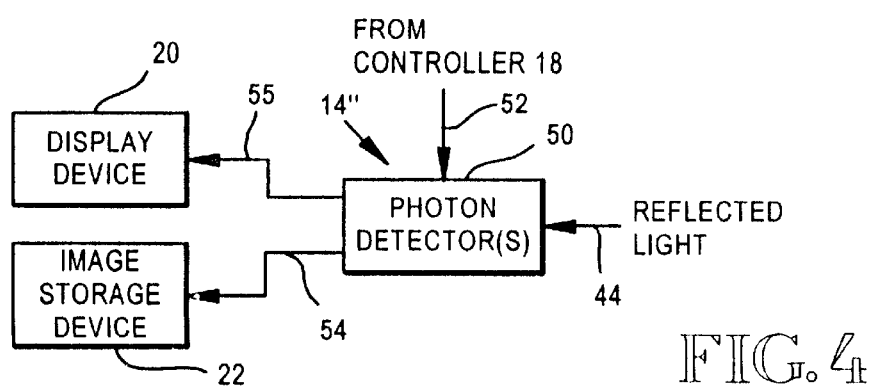

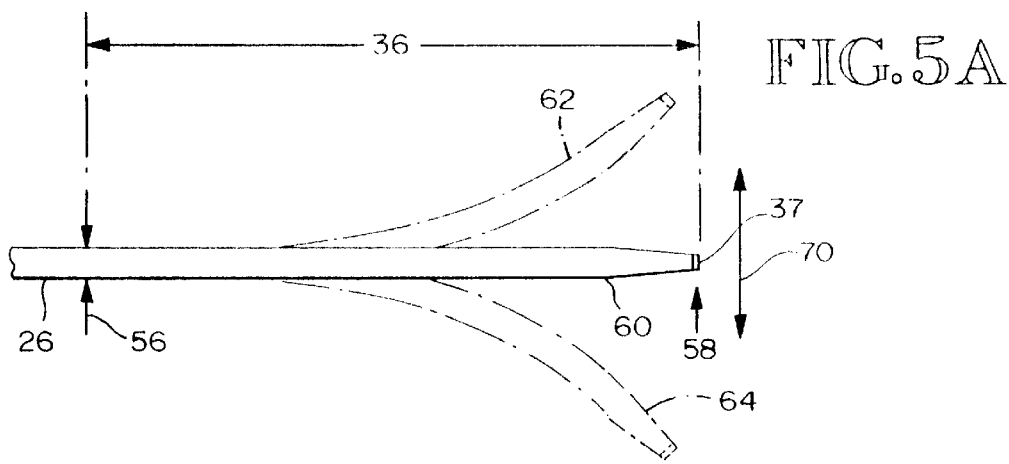
FIG. 5A
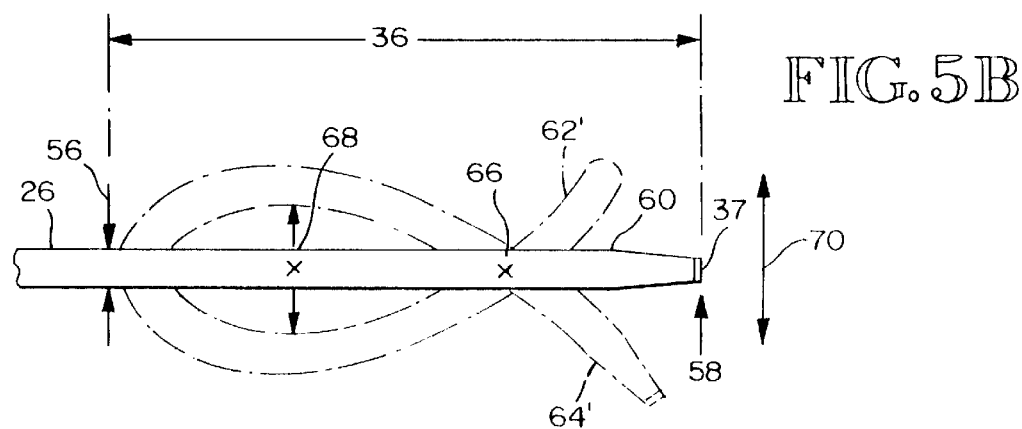
FIG. 5B
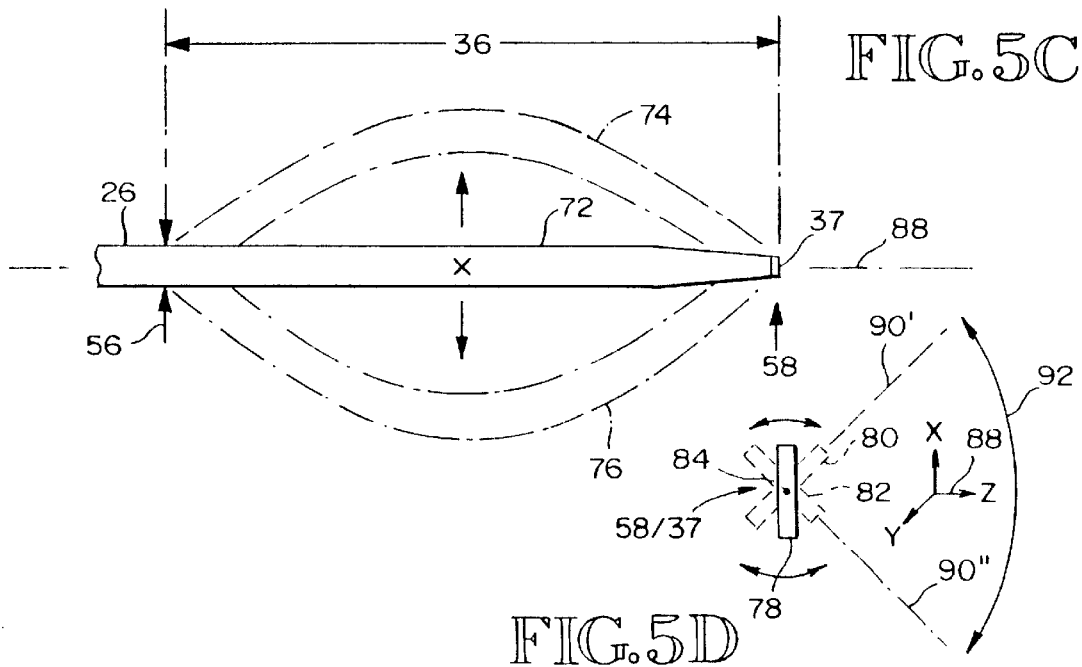
FIG. 5C
FIG. 5D

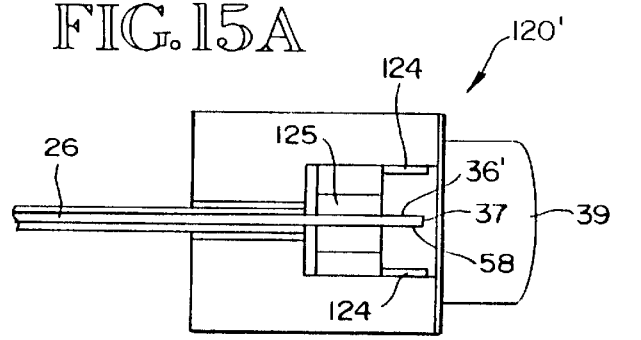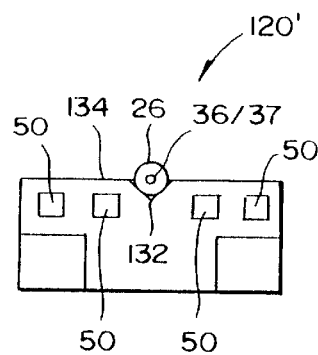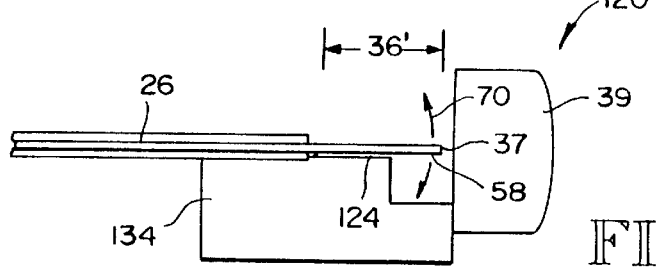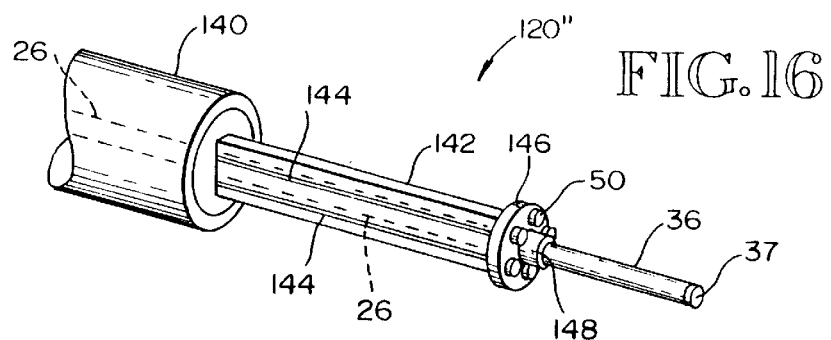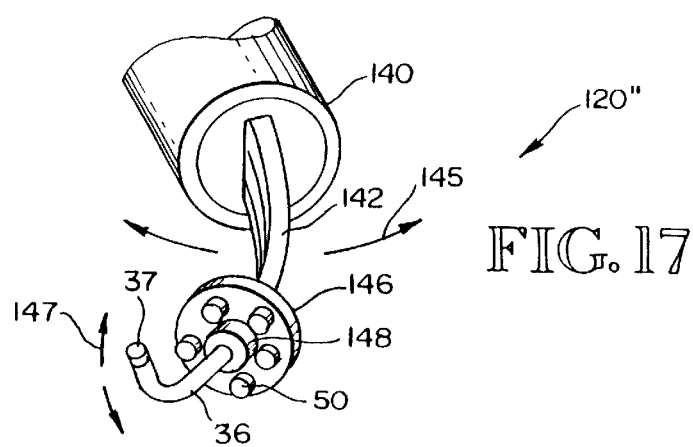

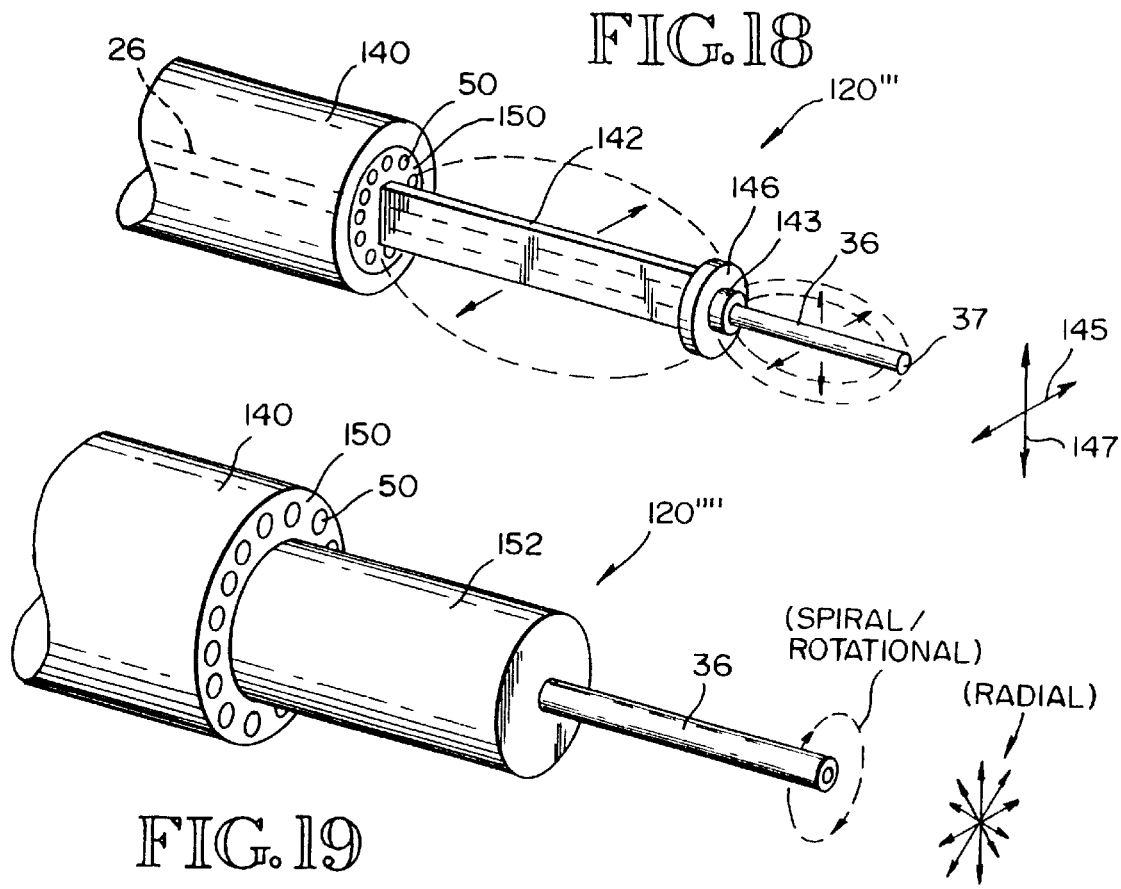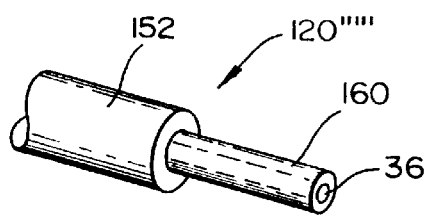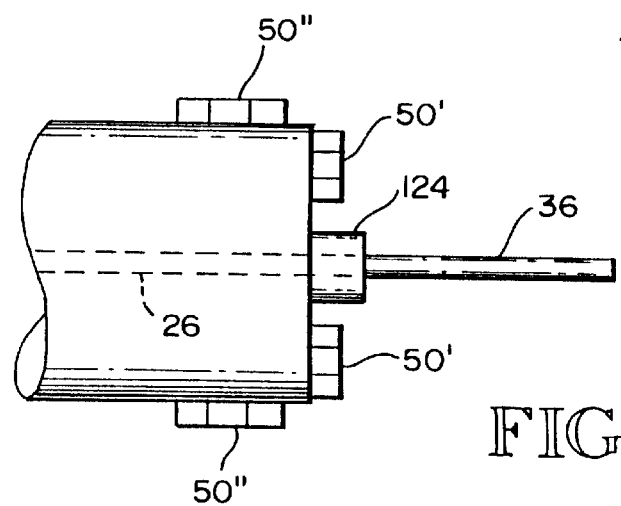

IMAGE ACQUISITION WITH DEPTH ENHANCEMENT

CROSS REFERENCE TO RELATED APPLICATIONS

This is a continuation in part of U.S. patent application Ser. No. 09/425,528 filed Oct. 22, 1999 of Seibel et al. for "Miniature Image Acquisition System Using a Scanning Resonant Waveguide," now U.S. Pat. No. 6,294,775 which in turn is related to U.S. Provisional Patent Application Serial No. 60/138,404 filed Jun. 8, 1999 for "Miniature Image Acquisition System Using a Scanning Resonant Waveguide." The content of these applications are incorporated herein by reference and made a part hereof.

BACKGROUND OF THE INVENTION

This invention relates to fiber optic scanning devices, such as fiber optic image acquisition devices and fiber optic image display devices, and more particularly to a fiber optic scanning device which enhances depth information, achieves a high image resolution and a wide field of view using a flexible fiber of very small diameter.

Fiber optic image acquisition devices include endoscopes, boroscopes and bar code readers. An endoscope is an imaging instrument for viewing the interior of a body canal or hollow organ. Entry typically is through a body opening. A boroscope is an imaging instrument for viewing an internal area of the body. Entry typically is invasive through a 'bored' opening (e.g., a surgical opening).

There are rigid endoscopes and flexible endoscopes. Rigid endoscopes do not have a pixelated image plane. Flexible endoscopes are smaller and conventionally have a pixelated image plane. Flexible endoscopes, however, are unable to achieve the resolution and field of view of rigid endoscopes. But the rigid endoscopes are unable to be used in many applications where small size and flexible fibers and shafts are required.

The goal of any endoscope is high image quality in a small package, allowing minimal tissue trauma. In the growing field of minimally invasive surgical techniques, there is great demand for smaller endoscopes that match current image quality. In particular, the demand for minimally invasive medical procedures has increased the demand for ultrathin optical endoscopes. However, commercial flexible endoscopes have a fundamental tradeoff of size versus image quality. The smaller the endoscope diameter the lower the image resolution and/or field-of-view (FOV), such that image quality deteriorates. Many endoscopic techniques are not possible or become risky when very small endoscopes are used because the doctor has insufficient visual information, i.e. small size and poor quality of images. Accordingly, there is a need for very small, flexible endoscopes with high resolution and FOV. This fundamental tradeoff of a flexible image generator that has both a very small diameter and has the high image quality is a major limitation in applications outside the human body, such as remote sensing.

Conventional flexible endoscopes and boroscopes include a large spatial array of pixel detectors forming a CCD camera. Typically a bundle of optical fibers capture an image and transmit the image to the CCD camera. To achieve a high resolution, wide field image, such CCD cameras often include a pixel detector array of approximately 1000 by 1000 detectors. For color fidelity it is common to include three such arrays, and where stereoscopic viewing is desired, this doubles to six arrays. A fiber is present for each pixel detector. Each fiber has a diameter greater than or equal to 4 microns. Thus, acquisition requires a space of greater than or equal to 4 microns per pixel. If a standard sVGA image is desired (800×600 pixels), then a minimum diameter of just the image conduit is greater than 3 mm. A 1000 by 1000 pixel detector array has a diameter of at least 4 mm. For a VGA standard, resolution and/or field of view is sacrificed by having fewer pixel elements in order to attain less than 3 mm overall diameter scopes. Reducing the diameter of the endoscope reduces the possible number of pixels, and accordingly, the resolution and field of view. Limits on diameter also limit the opportunity to access color images and stereoscopic images.

In the field of small (e.g., less than 3 mm dia.), flexible endoscopes, the scopes need to use the smallest pixel size, while still reducing the number of pixels, typically to (100×100). Note, these small flexible endoscopes are found by surgeons to be too fragile, so as not to be widely used. Instead doctors prefer small, but rigid-shafted (straight) endoscopes, greatly limiting their maneuverability and applicability.

In the field of large (e.g., greater than or equal to 4 mm dia.), flexible endoscopes, the scopes have a flexible shaft which is greater than or equal to 4 mm in diameter and typically include either a bundle of optical fibers or a small camera at the distal end to capture the image. However, there is still a tradeoff between the desired 50–70° FOV and image resolution at the full potential of human visual acuity until the scope diameter reaches >10 mm.

U.S. Pat. No. 5,103,497 issued Apr. 7, 1992 of John W. Hicks discloses a flying spot endoscope in which interspacing among fiber optics is decreased to reduce the overall diameter of the optical bundle. Rather than arrange a bundle of fibers in a coherent manner, in his preferred embodiment Hicks uses a multi-fiber whose adjacent cores are phase mismatched. The multi-fiber is scanned along a raster pattern, a spiral pattern, an oscillating pattern or a rotary pattern using an electromagnetic driver. The illumination fibers, the viewing fibers or both the illuminating fibers and the viewing fibers are scanned. In a simplest embodiment, Hicks discloses scanning of a single fiber (e.g., either the illuminating or the viewing fiber).

Hicks uses a small bundle or a single fiber to scan an image plane by scanning the fiber bundle along the image plane. Note that the image plane is not decreased in size. The smaller bundle scans the entire image plane. To do so, the bundle moves over the same area that in prior art was occupied by the larger array of collecting fiber optics. As a result, the area that Hicks device occupies during operation is the same as in prior devices. Further, the core size of the fibers in Hicks' smaller bundle limits resolution in the same manner that the core size of fibers in the prior larger arrays limited resolution.

One of the challenges in the endoscope art is to reduce the size of the scanning device. As discussed above, the minimal size has been a function of the fiber diameter and the combination of desired resolution and desired field of view. The greater the desired resolution or field of view, the larger the required diameter. The greater the desired resolution for a given field of view, the larger number of fibers required. This restriction has been due to the technique of sampling a small portion of an image plane using a fiber optic camera element. Conventionally, one collecting fiber is used for capturing each pixel of the image plane, although in Hicks one or more fibers scan multiple pixels.

When generating an image plane, an object is illuminated by illuminating fibers. Some of the illuminating light impinges on the object directly. Other illuminating light is scattered either before or after impinging on the object. Light returning (e.g., reflected light, fluorescent returning light, phosphorescent returnig light) from the image plane is collected. Typically, the desired, non-scattered light returning from an illuminated portion of an object is differentiated from the scattered light by using a confocal system. Specifically a lens focuses the light returning to the viewing fiber. Only the light which is not scattered travels along a direct path from the object portion to the lens and the viewing fiber. The lens has its focal length set to focus the non-scattered light onto the tip of the viewing fiber. The scattered light focuses either before or after the viewing fiber tip. Thus, the desired light is captured and distinguished from the undesired light. One shortcoming of this approach is that most of the illuminated light is wasted, or is captured by surrounding pixel elements as noise, with only a small portion returning as the non-scattered light used to define a given pixel.

Minimally invasive medical procedures use endoscopes which present a single camera view to the medical practitioner using a video monitor. The practitioner must mentally relate the flat, two dimensional image captured by the endoscope into the three dimensional geometry of the scanned target within the body. The trained practitioner adapts by using motion parallax, monocular cues and other indirect evidence of depth to mentally envision the geometry of the body. Improving the image presented to the practitioner is desirable. For example, current stereographic endoscopes (with two fiber bundles or cameras) provide additional image data, but exhibit sub-optimal performance. Achieving such improvement without adding substantial cost, weight and size to the endoscope continues to be a challenge.

SUMMARY OF THE INVENTION

According to the invention, a miniature image acquisition system having a flexible optical fiber is implemented. The flexible optical fiber serves as an illuminating wave guide which resonates to scan emitted light along a desired pattern. Preferably a single fiber is used for the illumination light. For multiple colors of illumination light, it is preferred that the light from the respective color sources be combined and passed through a distal tip of the single illuminating fiber for emission onto an object being viewed. In alternative embodiments multiple fibers, or concentric fibers, are used for the illumination light.

Rather than generating and sampling an image plane (i.e., in which pixels are spatially separated) as done for conventional flexible endoscopes and the like, an image plane need not be generated to capture an image by the scanner of this invention. Instead pixels are acquired temporally, being separated in time. An advantage of this approach is that image resolution is no longer limited by the detector size (e.g., the diameter of the collecting fiber). According to one aspect of this invention, image resolution, instead, is a function of the illuminating spot size. In particular image resolutions are improved by using a spot size which is smaller than the diameter of the collecting device. In one embodiment single-mode optical fibers are implemented which have smaller gaussian beam profiles and smaller core profiles allowing generation of smaller spot sizes at the scanned site.

Because a pixel is detected as the received light within a window of time, the photons detected at such time window come from the illuminated spot. Another advantage of this invention is that the confocal problem occurring in the prior art systems is avoided. Using a typical video rate, for example, to define the pixel time window sizes, one pixel is collected every 40 nanoseconds. For the light of one pixel to interfere with the light from another pixel, the light of the first pixel would have to bounce around approximately 20 feet on average (because light travels about 1 foot/nanosecond). For typical applications such light would have to bounce around in a space less than one cubic inch. That corresponds to approximately 240 reflections. It is unlikely that the light from one pixel will make 240 reflections before getting absorbed. Thus, the confocal problem is not significant.

According to one aspect of the invention, a distal portion of an illuminating fiber serves as a resonating waveguide. Such distal portion is anchored at an end proximal to the rest of the fiber, (e.g., referred to as the proximal end of the distal portion, or the proximal end of the resonating waveguide). The distal portion is free to deflect and resonate. The waveguide is flexible, being deflected along a desired scan path at a resonant frequency. Light detectors are positioned at the end of the illuminating fiber, (e.g., in the vicinity of the anchored proximal end of the distal portion). Note that collecting fibers may be present, but are not necessary. Further, the detectors may, but need not trace a scan pattern.

An advantage of the invention is that flexibility of the fiber, a wide field of view and high resolution are achieved even for small, thin scopes due to the method in which pixels are obtained, the presence of the lenses and the manner of driving the fiber. Because pixels are measured in time series and not in a 2-D pixel array, it is not mandatory to have small photon detectors. The size of the detector is not critical as in the prior scopes where many small detectors spanned a large area. Therefore, a scope of this invention can be made smaller than existing scopes while using fewer photon detectors that are larger than the pixel detectors of standard scopes. According to the invention, as little as one photon detector may be used for monochrome image acquisition and as few as single red, green and blue detectors may be used for full-color imaging. By adding additional detectors, the advantage of quasi-stereo imaging and photometric stereo is achieved accentuating topography in the full-color images.

According to another aspect of this invention, true stereoscopic viewing is achieved by measuring axial distance from the scope to the target by range finding at each pixel position. Such axial measurement is a third image dimension which is processed to generate stereo views.

According to another advantage of the invention, a single scanning fiber with a small flexible shaft provides (i) axial symmetry, (ii) a low cost method of providing color fidelity, increased object contrast and increased fluorescent contrast, and (iii) laser illumination useful for fluorescent imaging, medical diagnosis and laser surgery. These and other aspects and advantages of the invention will be better understood by reference to the following detailed description taken in conjunction with the accompanying drawings.

BRIEF DESCRIPTION OF THE DRAWINGS

FIG. 3 is a diagram of a collector subsystem and display portion of an embodiment of the image acquisition system of FIG. 1;

FIG. 4 is a diagram of a portion of another embodiment of the image acquisition system of FIG. 1, including a detector subsystem, display device and image storage device;

FIGS. 5A–C are diagrams of a resonant waveguide portion of the illuminating fiber of FIG. 2 in various resonance modes;

FIG. 5D is a diagram of a fiber's distal lens at varying orientations according to the resonance mode of FIG. 5C;

FIGS. 15A–C are planar views of a micro-optical electro mechanical system (MEMS) embodiment of a scope portion of FIG. 1;

FIG. 16 is a perspective view of another embodiment of a scope portion of the system of FIG. 1, including a bimorph bender actuator and in which photodetectors are mounted to a disk which moves during actuation of the bender;

FIG. 17 is a perspective view of the scope of FIG. 16 showing the fundamental mode of resonance for actuating members;

FIG. 18 is a perspective view of another embodiment of a scope portion of the system of FIG. 1, including a bimorph bender actuator in which photodetectors are mounted to a stationary base;

FIG. 19 is a perspective view of another embodiment of a scope portion of the system of FIG. 1, including a tubular piezoelectric actuator;

FIG. 20 is a perspective view of another embodiment of a scope portion of the system of FIG. 1, including a collector waveguide concentrically surrounding an illumination waveguide;

FIG. 21 is a planar view of a portion of a scope portion, including photon detectors positioned for differentially factoring out ambient light;

DESCRIPTION OF SPECIFIC EMBODIMENTS

Overview

Figure 1:
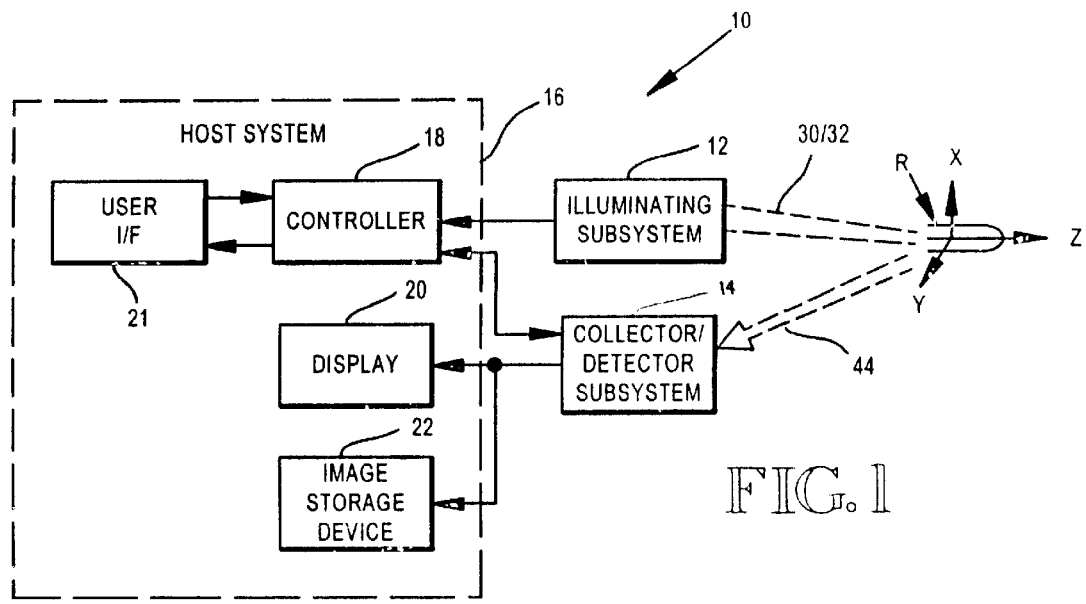
FIG. 1 is a block diagram of a miniature image acquisition system according to an embodiment of this invention.

Referring to FIG. 1, a miniature image acquisition system 10 includes an illuminating subsystem 12, a collector or detector subsystem 14 and in some embodiments a host system 16. The illuminating subsystem 12 emits light onto an object. The collector/detector subsystem 14 collects or detects light returning from the object. The illuminating subsystem 12 and collector/detector subsystem 14 are coupled to the host system 16. The host system 16 includes a controller 18 for synchronizing the illuminator subsystem operations and the collector/detector subsystem operations. The host system 16 also includes a display device 20, a user interface 21, an image storage device 22, a processor (not shown), and memory (not shown). The image acquisition system 10 in some embodiments is configured as a stand-alone device without a host system 16. In such a stand-alone embodiment the controller 18 and display 20 are part of the stand-alone system. In various applications, the miniature image acquisition system 10 embodies an endoscope, boroscope, bar code reader or another device for acquiring images. The term fibroscope is used herein to refer to an image acquisition system using a scanning fiberoptic waveguide.

Figure 2:
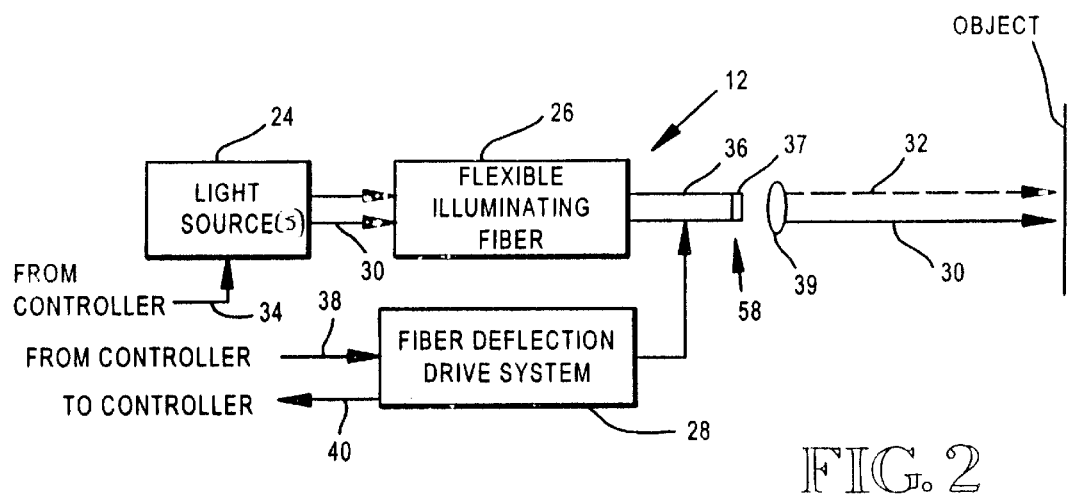
FIG. 2 is a diagram of the illuminating subsystem of the image acquisition system of FIG. 1.

Referring to FIG. 2, the illuminating subsystem 12 includes a light source 24, an optical fiber 26, and a fiber deflection drive system 28. The light source 24 emits a continuous stream of light 30 in one embodiment, and emits a stream of light pulses 32 in another embodiment. When pulses are implemented, the controller 18 sends a control signal 34 to the light source 24 to synchronize and control the timing of the pulse emissions.

The light from the light source 24 enters an optical fiber 26 and travels to a distal portion 36 where the light is emitted toward an object. The distal portion 36 is deflected and serves as a resonant waveguide 36. The fiber 26 or at least the distal portion 36 is flexible to withstand a resonant deflection motion at the distal portion. The controller 18 sends a synchronization signal 38 to the fiber deflection drive system 28, which in turn causes the distal portion of waveguide 36 to resonate. The resonant motion of the waveguide 36 causes the emitted light to be scanned over the object along a desired scan path. In some embodiments the control of the fiber deflection drive system 28 is a closed loop control with a sensor or feedback signal 40 being sent to the controller 18. In a preferred embodiment the drive system 28 is a piezoelectric drive system. In alternative drive system embodiments, a permanent magnet or electromagnet drive, an electrostatic drive, an optical drive, a sonic drive or an electrochemical drive are implemented in place of the piezoelectric drive.

Preferably one or more lenses 37 are formed at the distal end of the waveguide by shaping the distal end. Alternatively, one or more lenses are fused, bonded, mounted or otherwise attached to the distal end (i.e., the distal tip) of the distal end 36. Preferably, the lenses 37 do not extend beyond the circumference and diameter of the fiber end 36. The lenses 37 are fixed relative to the distal end 36 and move and change orientation with the distal end 36. These lenses 37 serves to collimate the emitted light. Another lens 39, such as a scan lens or an f-theta lens is positioned beyond the distal end 36 of the fiber in the path of the emitted light to focus the light on the object. In some embodiments the lens 39 is a refractive and/or diffractive optical element, such as a gradient refractive index lens. The lenses 37, 39 determine the image quality and define the image resolution of the subsystem 12.

The lens 39 serves as a scan lens and is formed of glass, plastic, or another waveshaping material such as liquid crystal. The optical power of the scan lens 39 determines at what distance, if any, an illumination forms a focal plane. If the emitted light 30/32 is collimated, the resulting image has a resolution approximating the emitted light beam diameter, resulting in an image with an enormous depth of field. Increasing the power of the scan lens 39 increases the pixel resolution while decreasing depth of field or depth of focus. The focal plane of the scan lens 39 depends on its power and location with respect to the distal tip 58 (see FIG. 5A) and distal lens 37. The focal plane can be adjusted by moving the scan lens 39 axially relative to the distal lens 37.

Referring to FIG. 3, in one embodiment a portion 42 of a miniature image acquisition system 10 includes a collector subsystem 14' and a retinal scanning display device 20'. Light from the illuminating system 12 (see FIGS. 1 and 2) is output to an object. Returning light 44 from the object is collected at the one or more collector fibers 46 and routed directly to a scanning display device 20'. In one embodiment the display device 20' scans the light onto the retina of a human eye E. In another embodiment the display device scans the light onto a projection screen, (e.g., being amplified electro-optically). In still another embodiment (not shown) the light from the collect fiber 46 is sampled and stored by an image storage device 27. The scanning or storage of the collected light is synchronized to correlate to the illumination light by controller 18.

In some embodiments the collector fiber 46 is deflected by a drive system 48 along a common path with the illuminating fiber 26 of the illuminating subsystem 12. The drive system 48 may be the same system as the illuminating subsystem drive system 28 or may be a separate drive system. Preferably the drive system 48 is a piezoelectric drive system. The drive system 48 receives the synchronization signal 38 from the controller 18. In embodiments where the collector fiber 46 is stationary, there is no need for a drive system 48.

The scanning display device is of the kind known in the art. An exemplary device is disclosed in U.S. Pat. No. 5,467,104 issued Nov. 14, 1995 for "Virtual Retinal Display" to Furness et al. Another exemplary device is disclosed in U.S. Pat. No. 5,694,237 issued Dec. 2, 1997 for "Position Detection of Mechanical Resonant Scanner Mirror" to Melville.

Referring to FIG. 4, in an alternative embodiment the miniature acquisition system 10 includes a detection subsystem 14". The detector subsystem 14" includes one or more photon detectors 50. Exemplary types of photon detectors 50 which may be implemented include photomultiplier tubes, silicon and semiconductor based photodetectors, electro-optically amplified optical fibers, image storage media (e.g., film) and photoemissive media. Returning light impinges on the photon detectors 50. The detectors 50 continuously, periodically or aperiodically sample the returning light 44 based upon on a sampling signal 52 received from controller 18. The sampling signal 52 correlates in timing to the synchronization signal 38 output to the illuminating subsystem 12. As a result, the photon detectors 50 output a continuous signal or a stream of electronic signal pulses corresponding to the sampling of the returning light 44. In one embodiment an output signal 54 is routed to an image storage device 22 to build and store an image frame of data. In various embodiments the image storage device 22 is an analog storage device (e.g., film) or a digital storage media. In addition, or alternatively, the same or a different output signal 55 is routed to a display device 20 to build and display a frame of image data. The display device may be any conventional display device, such as a cathode ray tube, liquid crystal display panel, light projector, gas plasma display panel or other display device.

Resonance Modes of the Illuminating Fiber Waveguide

Referring to FIGS. 5A–C the illuminating fiber 26 is shown being anchored at a point 56 along its length. The length of fiber 26 from the anchor point 56 to the distal tip 58 is referred to as the distal portion 36 which serves as the resonant waveguide. In some embodiments, a short fiber 26 is used in which substantially the entire fiber serves as the resonant waveguide 36, and occurs along the length from the anchor point 56 to the distal end 58. The waveguide 36 is driven by a fiber deflection drive system 28 (see FIG. 2) causing the waveguide to be deflected in a resonant mode.

There are many resonant modes which can be implemented by the drive system 28. In every mode, a stationary node occurs at the anchor point 56. An anti-node (i.e., point of maximum deflection) occurs along the length of the waveguide 36. Referring to FIG. 5A, a resonance mode is illustrated in which a stationary node occurs at the anchor point 56 and an anti-node occurs at the distal end 58. The waveguide 36 is shown in a neutral position 60, and at two maximum deflection positions 62, 64.

Referring to FIG. 5B, a resonance mode is illustrated in which there are two stationary nodes: one at the anchor point 56, and the other at a point 66 between the anchor point 56 and the distal end 58. An anti-node occurs at point 68 between the two stationary nodal points 56, 66. The waveguide 36 is shown in a neutral position 60, and at two maximum deflection positions 62', 64'. In various resonance modes, one or more stationary nodes are formed along the length of the waveguide causing the distal end 58 to swing along an arc 70. Zero up to n anti-nodes also may be formed where 'n' corresponds to either the number of stationary nodes or one less than the number of stationary nodes.

Referring to FIG. 5C, in a preferred resonance mode, a stationary node occurs at the distal end 58 of the waveguide 36. The waveguide 36 is shown in a neutral position 72, and at two maximum deflection positions 74, 76. Although no additional stationary nodes are shown between the stationary nodes at the anchor point 56 and at the distal end 58, in various embodiments additional stationary nodes do occur between such points 56, 58. To maintain a node of natural vibratory resonance at the distal tip of the waveguide, the mass and damping at the distal end 58 is a controlled design feature. Typically, a small increase in both mass and damping from the waveguide of uniform geometry and material properties is sufficient. One embodiment is the addition of a more dense (or larger) collimating lens 37 to the tip of the waveguide 36.

FIG. 5D shows a side view of the distal end 58 (e.g., lens 37) for the resonance modes having a stationary node at the distal tip 58. Shown are a neutral orientation 78 corresponding to the neutral position 72 of the waveguide 36, a maximum angular orientation 80 in one direction corresponding to the maximum deflection position 74, and another maximum angular orientation 82 in another direction corresponding to the maximum deflection position 76. As illustrated, a center point 84 is generally stationary for each orientation. In a precise illustration (not shown), the end 58 is slightly offset along the axis 88 (e.g., z-axis of FIG. 5D) of the waveguide 36, as the waveguide is deflected. However, there is no movement off the axis (along the x-axis or y-axis), only a change of orientation about the axis from orientations 78, to 80 to 78 to 82 and back to 78. Such changing orientation during the deflection of the waveguide 36 results in emission of a ray 90 of light in a direction generally perpendicular to a distal face of the lens 37. The ray 90 scans an arc 92 during the changing orientation of the distal end 58 and lens 37. Ray 90' is perpendicular to the lens 37 in position 82. Ray 90" is perpendicular to the lens 37 in position 80. Such arc 92 defines the field of view for the illuminating subsystem 12.

An advantage of placing a stationary node at the distal end 58 of the waveguide 36 is that the diameter of the endoscope or other illuminating device need not be enlarged to encompass a swinging arc 70 as in the resonant modes shown in FIGS. 5a and 5b. By fixing the distal end in X-Y space, rather than swinging it as a point source of light along a line or arc in X-Y space, optical distortions and aberrations are reduced. Further, rather than moving the distal end along an arc 70 to define the field of view, the position of the distal end 58 is substantially fixed while the orientation of the distal end changes with the resonating motion of other regions of the resonating waveguide. The changing angular orientation of the fiber distal end 58 defines the width of the field of view which is scanned (i.e., defines the arc 92).

Temporally Spaced Pixel Acquisition Method

One of the distinctions of the miniature image acquisition system 10 over prior art devices is that pixel resolution is determined by the illumination spot size, rather than a sampled spot size (e.g., by the sampling area of a sensor or collector fiber). In applicant's method, the illumination spot size, rather than the sampled area size, determines the pixel resolution. As a result, the detector size does not effect image resolution. Thus, one large detector or a plurality of smaller detectors are used according to the desired functionality, (e.g., color, stereo, high contrast).

Figure 6A:
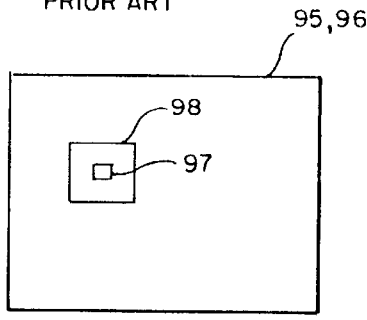
FIG. 6A is a diagram depicting sampling of a small pixel area of an image plane according to a conventional technique in which the sampled area defines the pixel size and pixel resolution.

Referring to FIG. 6A, conventionally a fiber illuminates an entire object area 95, either all at once or by scanning the object to form an image plane 96. The image plane is a spatial area of image pixels. In some conventional techniques the entire object area 95 is illuminated concurrently, while a small spatial area 97 of the image plane 96 is sampled to acquire an image pixel. In other conventional techniques, a light is scanned over the object to illuminate a changing portion 98 of the object. A small spatial area 97 within the illuminated area 98 is sampled to acquire the pixel. These conventional techniques are characterized by (i) a small spatial area being sampled which becomes the acquired pixel and determines the pixel resolution; and (ii) an illumination area larger than the sampled area for any given sample.

Figure 6B:
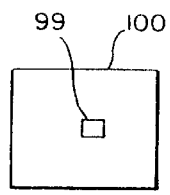
FIG. 6B is a diagram depicting sampling of a large area according to an embodiment of this invention in which a smaller illuminated area within the large sampled area defines the pixel size and pixel resolution.

Referring to FIG. 6B, a different technique is performed. According to an aspect of this invention, instead of illuminating a large area and sensing a small pixel area, a small pixel area is illuminated and a large area is sampled. Specifically, the light emitted by waveguide 36 (of FIG. 2) illuminates a small area 99 at some given time which corresponds to the pixel being acquired. The area 100 sampled by the detectors 50 or collector fiber 46 is larger than the illuminated spot size 99. This distinction is significant in that conventional techniques define their pixel and pixel resolution by the sampled area determined by their sensor (e.g., the sample spot size). According to this technique the pixel resolution is defined by the size of the illumination spot. The size of the illumination spot is precisely controlled by the waveguide 36 with lenses 37 and 39.

To have the illumination spot size correspond to the pixel to be sampled, there is a time synchronization between the illumination and the sampling. This synchronization is not to synchronize sampling to a specific location within an image plane as in the conventional method, but instead is a time synchronization to an illumination signal or pulse. For example, photon detectors 50 in one embodiment detect light from an entire object at any given time. The light detected at such detectors 50 is synchronized to a specific emission of light to obtain the pixel corresponding to that emission. In effect the spatial relationship is factored out of the sampling process. Instead, the pixel location is inherently known by knowing the position of the illuminating spot at the corresponding time.

By knowing the position of the scanned light spot for every instant in time, the image is generated one pixel at a time, much like a video signal. For example, by scanning image lines at 15.75 kHz and detecting the light at 12.5 MHz time resolution, the pixel stream composing a RGB color image at VGA resolution (640×480) is generated at video rates (60 Hz).

Using the time synchronization approach, a pixel is acquired within a given window of time. Because a pixel is detected as the received light within a window of time, the photons detected at such time window come from the illuminated spot. Further, by using multiple sensors, a common mode rejection scheme is implemented to filter out ambient light and detect the illuminated light returning back from the object.

An advantage of this approach is that the confocal problem occurring in the prior art systems is avoided. For example to define the pixel time window sizes using a typical VGA video rate, one pixel is collected every 40 nanoseconds. For the light of one pixel to interfere with the light from another pixel, the light of the first pixel would have to bounce around approximately 20 feet on average (because light travels about 1 foot/nanosecond). For typical applications such light would have to bounce around in a space less than one cubic inch. That corresponds to approximately 240 reflections. It is unlikely that the light from one pixel will make 240 reflections before the photon is absorbed or the photon flux is highly attenuated. Thus, the confocal problem is not significant.

Figure 7:
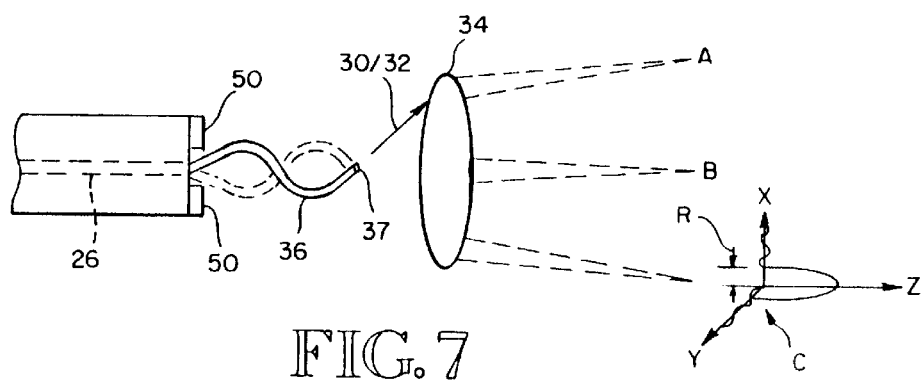
FIG. 7 is a diagram of the resonant waveguide and focusing lens showing points along a scan line and a corresponding illuminated spot.

Referring to FIG. 7, the waveguide 36 resonates while light 30/32 is emitted toward lens 39. The lens directs the light toward a specific spot location on a target object. At one extreme end of the waveguide deflection, a spot A of the object is illuminated. As the deflection continues the waveguide reaches a neutral position at which spot B is illuminated. Still continuing the waveguide reaches an opposite extreme at which spot C is illuminated. The light which illuminates spot C has a peak intensity radius R. Such intensity trails off outside the radius and is considered insignificant. Accordingly, a single scan line traverses a path from spot A to spot C. In some embodiments the fiber deflection system 28 is a linear scanning system which scans along a line. In another embodiment, the system 28 scans along a rectilinear or radial raster pattern. In still other embodiments, a spiral scanning pattern is implemented by the drive system 28, in which the radius of the spiral varies to trace an area of an object. The arc formed by points A and C determines the field of view, and may span to approximately 180 degrees. The distance of spots A, B, and C is determined by the lenses 37, 39 and may be substantially greater than the distance between the lenses 37, 39.

Figure 8:
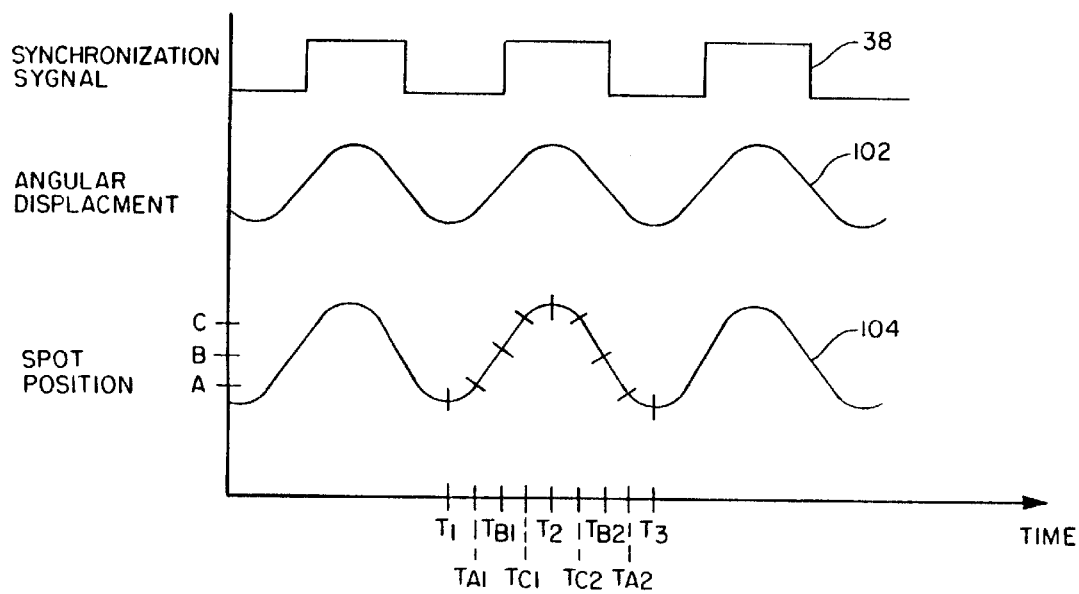
FIG. 8 is a chart of the fiber drive system synchronization signal, the angular displacement of the fiber tip and the illuminated spot position versus time.

Referring to FIG. 8, an exemplary synchronization signal 38 received from the controller 18 is shown for synchronizing the drive system 28. The angular displacement 102 (e.g., orientation) of the distal end 56 and lens 37 also is shown in FIG. 8. Lastly, the position 10 of the illuminating spot is shown as it is traced along a scan line of the object. An exemplary scan line, for example occurs from time $T_1$ to $T_2$. The next scan line (for an interlaced scanning embodiment) occurs from time $T_2$ to $T_3$. At various times during the scanning motion the illumination spot is over spots A, B and C. During the first scan line, spot A is illuminated at time $T_{A1}$. Spot B is illuminated at time $T_{B1}$. Spot C is illuminated at time $T_{C1}$. For the subsequent scan line occurring from time $T_2$ to $T_3$, a corresponding spot C is encountered first and illuminated at time $T_{C2}$. After corresponding spot B is illuminated at time $T_{B2}$. Then corresponding spot A is illuminated at time $T_{A2}$.

For a VGA resolution implementation, the time from $T_1$ to $T_3$ is 63.5 µs (microseconds). Thus, the time from $T_1$ to $T_2$ is 31.75 µs. The time from $T_{A1}$ to $T_{C1}$, is less than 31.75 µs. Specifically, for a VGA standard each scan line is divided into 800 equally times pixels. Thus, each pixel spans 40 ns (nanoseconds). Accordingly, the time from $T_{A1}$ to $T_{C1}$ is 25.6 µs.

Figure 9:
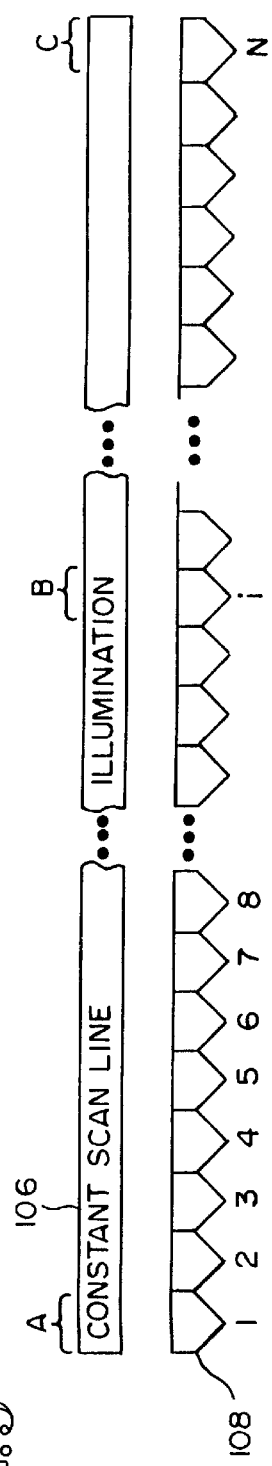
FIG. 9 is a diagram of a scan line formed by constant illumination which is continuously sampled, wherein the sampling result is divided in time to derive N pixels.
Figure 10:
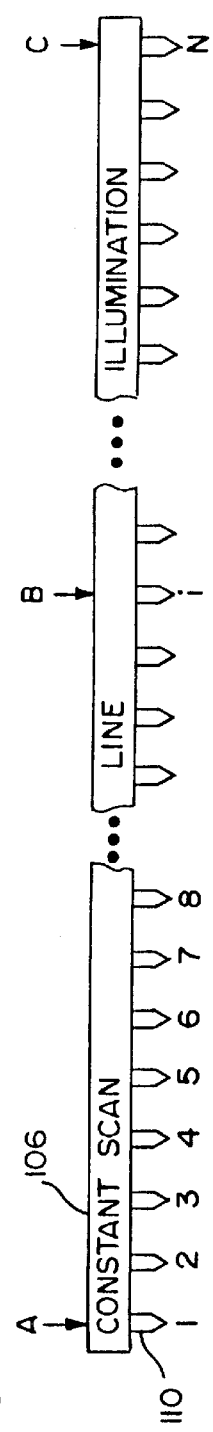
FIG. 10 is a diagram of a scan line formed by constant illumination which is periodically sampled, wherein each sample corresponds to one of N pixels.

FIGS. 9 and 10 depict an implementation in which the emitted light is a continuous stream of light 30 which moves along a scan line 106. In the FIG. 9 implementation the photon detectors 50 are continuously active with a pertinent portion ($T_A$ to $T_C$) being divided equally into 'N' pixels 108. For the VGA standard there is a 40 ns sampling time per pixel. For another standard, a different sampling time may be used. In the FIG. 10 implementation the photon detectors 50 are sampled periodically. Each sampling corresponds to an acquired pixel 110. 'N' pixels are acquired per scan line 106. In one embodiment, each sampling occurs over a duration of 20 ns. The time between midpoints of each sampling interval is 40 ns. for a VGA standard. For such standard, a corresponding sampling time interval is 10 ns. Again alternative sampling times and time intervals may be used.

Figure 11:
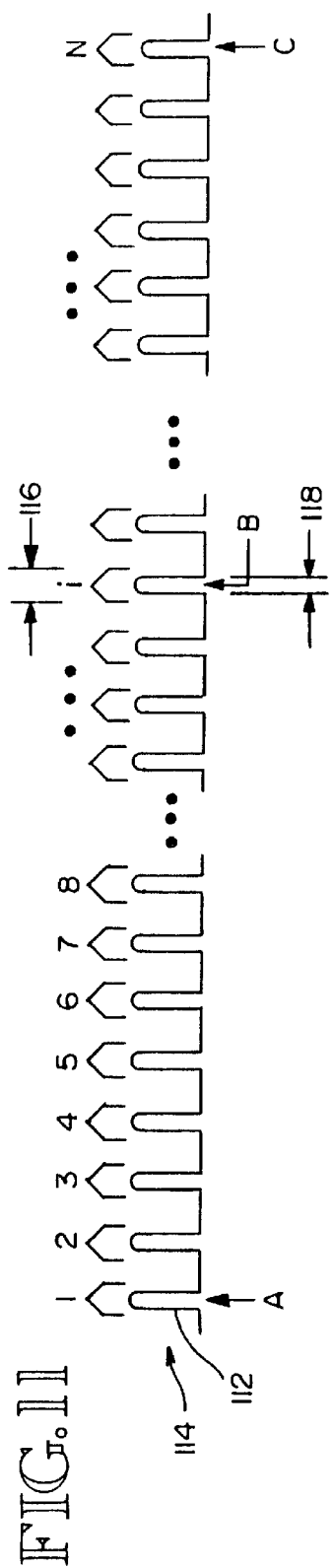
FIG. 11 is a diagram of a scan line formed by periodic pulsed illumination, in which periodic sampling is performed in synchronization with the pulses to derive samples of N pixels.

Referring to FIGS. 2 and 11, in one embodiment the illumination system 12 emits pulses 112 of light 32 periodically during scanning of a scan line 114. The photon detectors 50 (see FIG. 4) are synchronized to sample the object or an area of the object including at least the illuminated spot at a time to capture the returning light corresponding to a known spot. The sampling interval, i, corresponding to a spot (e.g., spot B) spans a time period 116 which is any of greater than, equal to or less than the time interval 118 of the light pulse for the spot. A typical time for the sampling interval 118 is 20 ns, and may vary. In still another embodiment (not shown) the detectors 50 continuously detect the returning light as described regarding FIG. 9, while the sampling results are correlated to the emitted light pulses 112.

By maintaining the illumination and/or detector at a fixed frequency, (e.q., 1/40 ns=12.5 MHz), the signal to noise ratio can be increased significantly with amplification at only the fixed frequency. Thus, noise at all other frequencies can be eliminated by filtering at higher and lower frequencies.

Physical Embodiments

Figure 12:
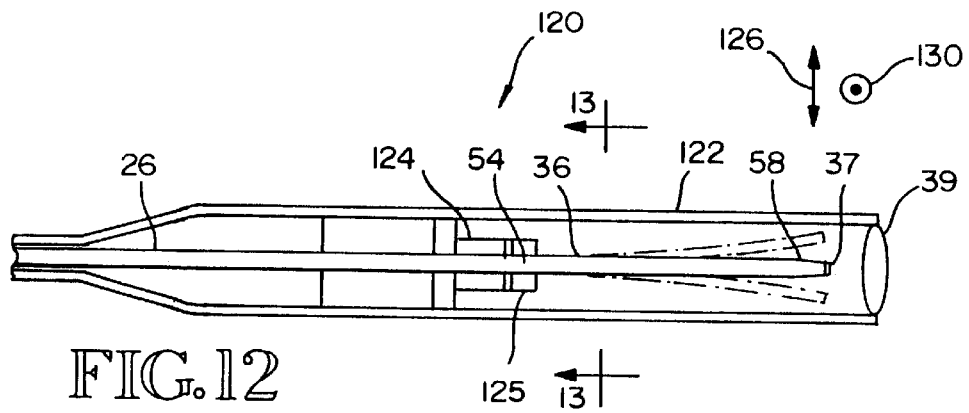
FIG. 12 is a planar side view of a scope portion of the system of FIG. 1.

Referring to FIG. 12, a scope portion 120 of the image acquisition system 10 is shown in which the waveguide 36 and an actuator 125 of the fiber deflection system 28 are enclosed in a protective sheath 122. The scan lens 39 seals the end of the scope. The focal plane of the scan lens 39 depends on its power and location with respect to the fiber tip 58 and distal lens 37. The focal plane can be adjusted by moving the lens 38 axially relative to the distal lens 37.

Figure 14:
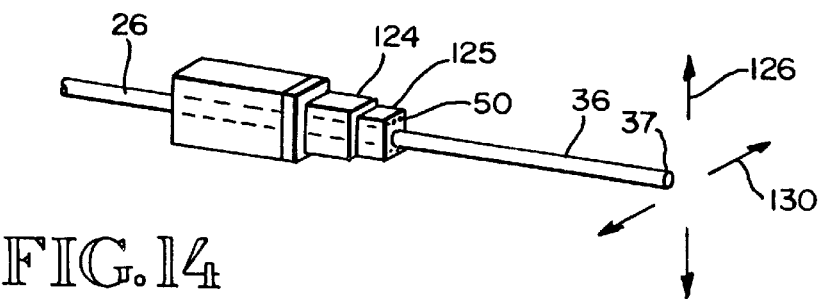
FIG. 14 is a perspective view of the scope of FIG. 13 without an outer sheath.

For single axis 126 scanning the waveguide 36 is deflected within the sheath 122 by the actuator 125. The base of the cantilevered waveguide is anchored to the distal end of the actuator 125 creating the first stationary 'node' of the vibratory resonance. Any of the resonance modes described with regard to FIGS. 5A–D may be implemented. For two axis scanning a second actuator 124 deflects the scope 120 along an axis 130 (see FIG. 14). In some embodiments, however, the actuators 124 and/or 125 produce a nonlinear actuation of the waveguide to induce two dimensional motion, such as along a spiral pattern.

Figure 13:
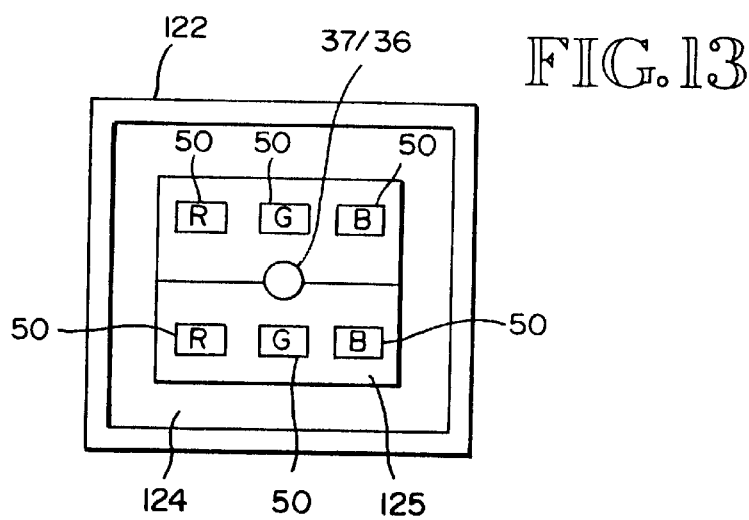
FIG. 13 is a planar front view of the scope of FIG. 12.

Referring to FIG. 13, pairs of red, green, and blue photodetectors 50 are shown within the distal anchoring surface of actuator 125 to capture color images in quasi-stereo. The photodetectors temporal bandwidth is higher than the rate of pixel illumination to avoid limiting contrast or resolution. For example, such photodetector bandwidths are $\geq$12.5 MHz for VGA and $\geq$19.8 MHz for sVGA video standards. Many silicon-based photodiodes that are smaller than 1 mm diameter have sufficient bandwidth in the visible spectrum. For increased noise reduction, the photodetectors are combined with integrated pre-amplifiers in a Micro-optical Electro Mechanical Systems ('MEMS') fabrication process. An alternative approach is to guide the light to the proximal end of the scope within the outer concentric layer or specialized cladding of the single fiberoptic cantilever, or by using one or more large core (multimode) optical fibers to capture the backscattered light. Such arrangements allow the photodetectors to be at the proximal end of the scope, which would be less affected by the environmental factors, physical space limitations, and the possible complications brought on by the desire for disposability and/or sterilizability.

Referring to FIGS. 15A–C, a 'MEMS' embodiment of the scope portion 120' of system 10 is shown. In such embodiment the optical waveguide structure for mechanically resonant vibratory motion is batch fabricated using silicon micromachining techniques, producing a MEMS scanner. In such embodiment the actuators 124, 125, detectors 50 and additional light conduits (not shown) also are fabricated using the same MEMS processes resulting in an integral structure. A microlens 37 and scan lens 39 also are fabricated using the same MEMS processes, or a separate injection/pressure molding or MEMS process, then is attached to the other MEMS structure. Additional optical and displacement sensors also may be incorporated in the scope 120' for long-term control of the scanning stability. In such embodiment the MEMS cantilevered waveguide 36' is being illuminated from an optical fiber 26 that is bonded within a V-groove 132 of an underlying substrate 134.

Referring to FIGS. 16 and 17, in an alternative embodiment of a scope portion 120", the optical fiber 26 extends through a tubular mechanical support 140, which serves as a conduit for electrical wires and optical fiber(s), and support a surrounding protective sheathing (not shown). A piezoelectric bimorph bender 142 is cantilevered out from the support 140, along with the electrical wires 144 and optical fiber 26. The bender 142 serves as the actuator of the fiber deflection drive system 28 (see FIG. 2). At a distal end of the bender 142 is a disk structure 146 that supports the cantilevered fiberoptic scanning waveguide 36 used to generate a slow scan axis 145.

On the disk structure 146 are the photon detectors 50, such as commercial 0.1 mm diameter photodiodes that are bonded directly onto the disk. At the center of the detectors 50, surrounding a base of the waveguide 36 is a piezoelectric ring 48 which drives the fiberoptic waveguide 36 into vibratory resonance. The scanning motion of the two piezoelectric actuators 142, 148 produces scanning in two orthogonal directions 145, 147 simultaneously. The fundamental mode of resonance is shown in FIG. 17 for both scan axes 145, 147.

Referring to FIG. 18, in a similar scope 120''' embodiment rectilinear scanning motion in a reduced diameter is achieved by using a second mode of vibratory resonance for both scan axes 145, 147. Like in the FIG. 17 embodiment the bimorph bender 142 is deflected. In this second mode, however, another stationary node occurs in the scope. Specifically, in the FIG. 18 embodiment a second node of vibratory motion occurs at the distal end of the vibrating elements 142, 36. For example, the additional mass of a collimating lens 37 at the fiber tip allows the motion of the scanned beam to be rotational without translation. Note, the photon detectors 50 are located a stationary base 150 of the scope 120'''.

Referring to FIG. 19, in yet another scope 120'''' embodiment, two rotationally symmetric scanning motions of the waveguide 36 are achieved using a single actuator 152. For either of a circular scanning and radially scanning implementation, actuator 152 is a tube piezoelectric actuator.

Referring to FIG. 20, in yet another scope 120''''' embodiment, the illuminating waveguide 36 is concentrically surrounded by a collector waveguide 160. In this embodiment the collector waveguide 160 moves with the deflector waveguide 36. Such arrangement results in spatially filtering out reflections from multiple reflections that would otherwise degrade resolution and color fidelity.

Stereo and Color Viewing

The various scope embodiments may be adapted to enable stereoscopic and color viewing. Stereo imaging for example is implemented by providing multiple detectors which are physically separated and which synchronously sample the returning light. This is a substantial advantage over prior systems in which a separate scope is used for stereoscopic viewing. In contrast, a single illuminating fiber is used to obtain stereoscopic viewing.

Color viewing is implemented by including photon detectors sensitive to respective ranges of wavelengths corresponding to the desired colors. Referring to FIG. 13, matched pairs of red, green and blue photodetectors are included for stereoscopic color imaging.

In the various embodiments the photon detectors 50 may be single or multi-element photon detectors. Referring to FIG. 21, photon detectors 50', 50'' are mounted at different axes so as to differentially factor out photons of ambient light (and highly scattered back reflections from the illumination of the target), as distinct from the photons emitted by the illuminating fiber 26 and returning directly back by the object. In particular, common mode rejection of ambient light is implemented for embodiments in which the scope is exposed to ambient light having an intensity which is significant relative to an intensity of illuminated light 30/32. This has the advantage of improving color fidelity.

Consider that color changes upon each reflection. Capturing the light after striking many surfaces results in scrambled pixel color. Also, the multiple reflections degrade the image resolution and contrast due to the other target structures affecting the light. Accordingly, it is desirable to capture the color returning back from the first point the light strikes.

The arrangement of photodetectors 50' and 50'' in the FIG. 21 embodiment on the sides and axially in line with the illumination light allows for rejection of the background component. As a result, color fidelity and image resolution are improved.

In some embodiments polarization maintaining illumination components and polarization filters are included to reject backscattered light that has undergone multiple scattering and color shifting. The quasi-confocal arrangement of the detectors in FIG. 20 together with polarization filters also results in improved color fidelity and image resolution.

Method of Depth Enhancement

When acquiring an image with a fibroscope with a single detector, the image has a viewpoint that appears to be located at the position of the illuminating fiber and a single apparent directional light source that appears to be located at the position of the light detector that senses the returning light. The image has strong depth cues resulting from the single apparent light source. Depth cues can be enhanced by using images captured from a multitude of sensors. These images can be combined to form an improved image with enhanced shadow detail or depth perception.

Changing the position of the detector does not change the position of the image viewpoint. Changing the position of the detector, however, does change the apparent lighting condition. Significantly, with a multitude of detectors, the shadows in the images created by one detector differ from the shadows in the images created by another detector located elsewhere. Images from any combination of sensors can be combined to provide a variety of lighting schemes best suited for the viewing conditions. By obtaining a sequence of images with the plurality of detectors 50, either located at the distal end or at the proximal of light collecting optical fibers (see FIGS. 15–21), motion images with dynamic lighting are attained.

Other information gathered from a variety of sensors also is incorporated into the images. In one embodiment the light detectors from each of at least three detectors is visible monochromatic or color light. In other embodiments, one or more of the at least three sensors captures non-visible light (e.g. ultraviolet, infrared) coincidentally output by the waveguide (e.g., an ultraviolet or infrared beam is passed through a common waveguide with the visible light). Alternatively, other contrast mechanisms including fluorescence or polarization are included.

Rather than enhancing depth cues, depth information for each pixel is derived using images from at least two detectors and preferably from at least three detectors using photometric stereo techniques. To use photometric stereo, the images have the same viewpoint with no relative motion, ideally simultaneously acquired, but with different single source lighting positions. These types of images are readily attainable with the fibroscope. In contrast, to achieve the necessary images, current endscopes require multiple lighting channels and would acquire the images sequentially with only a single lighting channel illuminated at a time. Movement in the endoscope or surface between image acquisitions, however, introduce inaccuracies in the derived depth information from such endoscopes.

When at least three detectors' corresponding images are used to derive the depth information, the three dimensional shape is accurately derived without the need for additional information. When only one detector is used, certain assumptions are made and user assistance is required to accurately derive the three dimensional shape. When only two detectors are used, user assistance is reduced, but assumptions of surface properties are made to achieve accurate depth detail. Accordingly, at least three detectors are preferable to avoid user assistance in deriving accurate depth information. The use of multiple images to derive depth information removes the ambiguities of whether a surface is concave or convex, and allows analysis of a surface with varying albedo (i.e., surface diffuse reflectance properties).

With just one or more detectors two dimensional image features are readily attained. Depth cues in the image exist, especially from shading and shadows, but due to the relative proximity of the illumination fiber and the detectors (i.e. the apparent viewpoint and apparent lighting direction) these cues may be insufficient. By extracting the depth information, depth cues are enhanced by calculating the effects of a change in viewpoint or a change in lighting direction, even those physically unobtainable due to the geometry of the fibroscope.

Figures 22, 23:
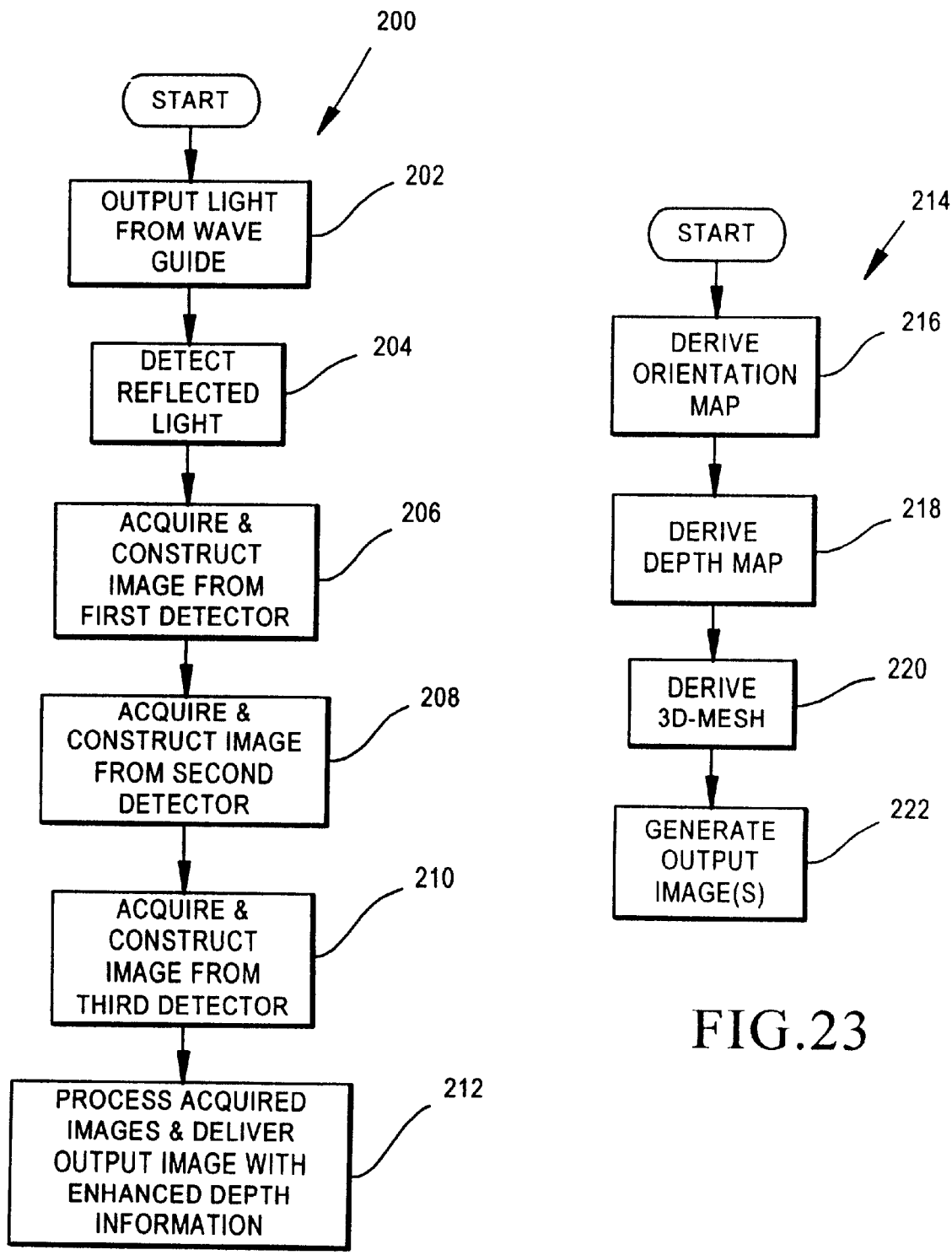
FIG. 22 is a flow chart of a method for acquiring an image with enhanced depth information according to one embodiment of this invention.
FIG. 23 is a flow chart of a image processing according to one embodiment of this invention.

Referring to FIG. 22, a flow chart for a method 200 for generating an output image with enhanced depth information is presented. At step 202, a beam of light 30/32 is output from a resonant fiber waveguide 36 (see FIG. 2). The waveguide 36 scans the output beam along a scan path. A scan lens 39 focuses the beam onto the an object's surface (i.e., target). At a given time the beam is focused to impinge on a spot of the target, the spot being an illuminated spot, the illuminated spot varying with time as the beam is scanned along the target surface.

At step 204, returning light from the target surface is detected by the plurality of detectors 50. One detector has a first location relative to the resonant fiber waveguide 36. Another detector has a second location relative to the resonant fiber waveguide. A third detector has a third location relative to the resonant fiber waveguide. The returning light is detected concurrently at each of the detectors 50.

At step 206, a plurality of pixels for a first image are acquired from the returning light detected by a first detector. At step 208, a second plurality of pixels for a second image are acquired from the returning light detected by a second detector. Similarly, at step 210 a third plurality of pixels for a third image are acquired from the returning light detected by the third detector, and so on for each detector. Preferably, such images are acquired and constructed concurrently.

Because the light being returning originates from a common point (e.g., the end of the waveguide 36), the images acquired at each detector 50 have a common apparent viewpoint. However, because each detector has a different location, each image acquired has a differing apparent lighting direction. The first image has a first apparent lighting direction based upon the first detector's location. The second image has a second apparent lighting direction based upon the second detector's location. The third image has a third apparent lighting direction based upon the third detector's location.

At step 212 the acquired plurality of images are processed to derive an output image of the target surface, including depth information based upon the differing apparent lighting directions of at least two, and preferably at least three, of the plurality of detectors 50.

In a color image acquisition system the output beam of light is a combination of a first color light beam, a second color light beam and a third color light beam (e.g. red, green, and blue). In such embodiment the acquired image from a given detector as discussed above, instead is acquired from three detectors—one for each of the three colors of the output beam. Previously, it was described that two and preferably three images were acquired to be processed for generating the depth information. These images do not need to be color. With three co-located detectors being used per acquired image in a 3-color imaging system, and two additional multi-wavelength to achieve the preferred three images for depth extraction, means that preferably at least five detectors are used to acquire the 3 color output image with enhanced depth information.

Referring to FIG. 23, a flow chart of the method 214 for processing the acquired images is presented. At step 216, an orientation map (also known as a needle map) of target surface normals is generated based upon the plurality of acquired images. At step 218, a depth map is obtained from the orientation map. At step 220, a 3-dimensional mesh is obtained from the depth map. In an alternative embodiment, a gaussian image (discrete histogram) is obtained instead of the depth map. The gaussian image then is used for image recognition applications.

At step 222 an output image is generated with enhanced depth information. For example, the depth information in the 3-dimensional mesh is used to add virtual shadows to better contrast the depth cues in the output image seen by a viewer. In one embodiment, two stereographic images are derived from the 3-dimensional mesh in which a viewer's binocular disparity is calculated. Each image is output to a respective eye of the viewer.

With regard to step 216, an orientation map indicates surface orientation for each pixel and is useful for recovering the shape of an object being imaged. Generally, the mapping between brightness and surface orientation is not unique because brightness has one degree of freedom and surface orientation has two degrees of freedom. (Although, for special points, such as those pixels where the brightness is a maximum or a minimum, surface orientation typically can be determined uniquely from a single sample.)

To recover the surface orientation for a contoured surface, additional information is needed beyond the single brightness value of an acquired pixel. Two images acquired with different lighting provide two samples to use in solving for the orientation value with the two degrees of freedom. Even with two images, however, the two resulting equations may be nonlinear, or the orientation may be derived only over a small range (where the relationship is linear). Preferably at least three images are acquired as discussed above to improve the accuracy of the orientation map and increase the range of possible surface orientations for which a solution can be achieved. The third image also is also preferable because it allows the depth analysis to be performed independent of variations in the albedo (surface diffuse reflectance property). The variation in albedo can also be computed using the third image.

When more than three sensors are available, the additional images can be used to improve the orientation estimates. Where 'n' images are obtained from 'n' photodetectors, one approach for determining orientation is by minimization, such as using the following equation:

$$e = \int\int_I ((f_x^2 + f_y^2) + (g_x^2 + g_y^2))dxdy + \sum_{i=1}^{n} \lambda_i \int\int_I (E_i(x, y) - R_i(x, y))^2 dxdy$$

where $E_i$ is the brightness measured in the i-th image and $R_i$ is the corresponding reflectance. The constants $\lambda_i$ are parameters that weight the errors in the irradiance equations relative to departure from smoothness.

The discrete equations for deriving the orientation values (f, g) are derived iteratively in one embodiment using the following equations:

$$f_{kl}^{n+1} = \overline{f}_{kl}^n + \sum_{i=1}^{n} \lambda_i (E_{i,kl} - R_i(f_{kl}, g_{kl}))\frac{\partial R_i}{\partial f}, \text{ and}$$

-continued $$g_{kl}^{n+1} = \bar{g}_{kl}^n + \sum_{i=1}^{n} \lambda_i (E_{i,kl} - R_i(f_{kl}, g_{kl})) \frac{\partial R_i}{\partial g}.$$

In other embodiments, a lookup table is used to determine orientation. The table is indexed by the observed brightness measurements in each image. The values of the table are the orientations selected based on equations or experiments on a known calibration object. By selecting values from the look-up table based upon observed brightness measurements, surface orientation values are obtained for each pixel of the target object being imaged. The collection of orientation information of the image acquired is referred to herein as the orientation map.

With regard to step 218, the depth map then is derived from the orientation map. A depth map represents the shape of the object in a different manner. Specifically, rather than specifying orientation information, the depth map specifies relative height above a reference plane. The depth map is a gray-scale image with black representing the lowest heights and white as the highest. The height z of a pixel (x,y), or z(x,y), is a function of the gradients of the corresponding orientation values f and g. Given f and g, the depth z can be recovered by integrating along arbitrary curves $$z(x, y) = z(x_0, y_0) + \int_{(x_0, y_0)}^{(x, y)} (f\, dx + g\, dy)$$

Along a closed path, the integral should equal zero. In practice, f and g are imprecise because they are recovered from noisy image data. Optimization techniques, such as global integration or iterative Laplacian relaxation techniques are able to recover smooth surfaces from noisy orientation maps.

With regard to step 220, the 3-dimensional mesh is derived from the depth map. The vertices of a planar mesh are displaced by an amount related to the gray scale pixel values of the depth map. This mesh can then be rendered from various viewpoints, lighting conditions, or surface properties (color derived) to give a better perspective or impression of the depth. The viewpoints and lighting conditions may be physically impossible given the geometry of the fibroscope. Further information derived from other sensors (infrared, ultraviolet, polarization) or from measurements (contour maps) can be included.

In some embodiments, an orientation histogram is obtained instead of the depth map. The orientation histogram, the discrete case of the extended gaussian image, is used in object recognition. Prototype orientation histograms of known shapes are obtained. Generally, the prototype orientation histograms of various objects will be significantly different. Experimentally obtained orientation histograms can then be compared with the stored prototypes to assign the unknown object to one of the known object types.

Additional shading or other image enhancement schemes also are applied in various embodiments to improve the image quality. For example, two output images are generated in one embodiment to present stereographic images to respective eyes of a viewer. The two images are rendered differently to account for a viewer's binocular disparity. The binocular disparity is calculated based upon the separation distance between the two eyes and the apparent distance to the surface. The separation distance is selectable in some embodiments and set to a standard average value in other embodiments. The apparent distance to the surface is selectable in one embodiment and set to a default standard distance in other embodiments.

Range-Finding

In another embodiment true stereoscopic viewing is achieved by performing an axial measurement from the scope to the target by range finding at each pixel position. Such axial measurement is a third image dimension which is processed to generate stereo views. For example, signals from matched pairs of detectors 50 are processed by the controller to detect phase difference in the returning light. Such phase difference corresponds to a range distance of a target object from the scanner.

In one implementation the illuminating subsystem 12 (FIGS. 1 and 2) includes a light source 24 (FIG. 2) which is formed by a visible light source and an infrared light source. The visible light and infrared light are emitted from a common illuminating fiber 26. Referring to FIGS. 4 and 15–20 the light detectors 50 include both visible light detectors and infrared light detectors.

The infrared light source preferably is a modulated laser infrared source which outputs infrared light in the GHz frequency range. Fast photon infrared detectors detect the returning infrared light. Preferably, the infrared photon detectors generate detection signals at the same frequency as the infrared light source. The phase difference in the modulation between the illuminated infrared light and the collected infrared light corresponds to the distance of the target pixel to resolutions of $\leq 1$ mm. In particular, for an embodiment in which the infrared light is modulated at 1 GHz, the infrared light travels 1 foot between pulses or about 1 mm per degree of the 360 degrees of phase difference between pulses.

Rather than measure the range of the target reflecting back the light in terms of phase as just described, in alternative embodiments the range of the target is measured in time or frequency, or by using optical feedback interferometry. In the time of flight method, the range determining output beam is emitted from a high modulation bandwidth laser diode. A short laser pulse is emitted at a given frequency (e.g., on the order of tens of kHz). For each pulse, the time elapsed between emission and receipt of the returning pulse is measured. The measured time is proportional to the distance between the detector and the closest point on the object surface.

Alternatively, a continuous laser emission scheme is used rather than the pulsed emission scheme where timing of samples received correspond to a specific time of emission of the laser light. Also, in some embodiments light is emitted from a directly modulated laser diode using a high modulation bandwidth of optical intensity. Distance is measured by sampling at a time period corresponding to the modulation to determine time elapsed between emission and receipt of corresponding returning light. The time elapsed is proportional to the distance to a closest point on the target surface.

In the frequency method an electronically tunable laser diode which can be frequency modulated continuously to determine short range sensing is used. A signal with a time-varying frequency modulates the range-finding output beam. The returning beam is mixed with a reference signal to produce a beat frequency which is a function of the distance to the target surface.

With regard to the optical interferometry method, back reflecting light along the path of the emitted light causes an interference pattern with the emitted light. In one embodiment injection detection methods are used to detect the phase or amplitude of the returning light signal. Self mixing, using a pulsed scheme correspondence to make a derivative of an optical power waveform allows for depth (D) to be determined as:

$$D = \frac{c}{4\left(\frac{dv}{dt}\right)}(\sigma_0 f_{bo} + \sigma_1 f_{b1})$$

where c is the speed of light, σ is −1 or +1 according to the motion of the target, and the f values are the beat frequencies of the output power with feedback during upward and downward ramps of the frequency shift.

In each method a fast or high bandwidth photon detector at infrared or near infrared frequency ranges is included for detecting the returning light. In addition, it is preferable to use low dispersion fiberoptics, fiber couplings with low back reflection losses, fast timing and/or phase shift circuitry, along with averaging software to increase signal to noise ratio.

Figure 24:
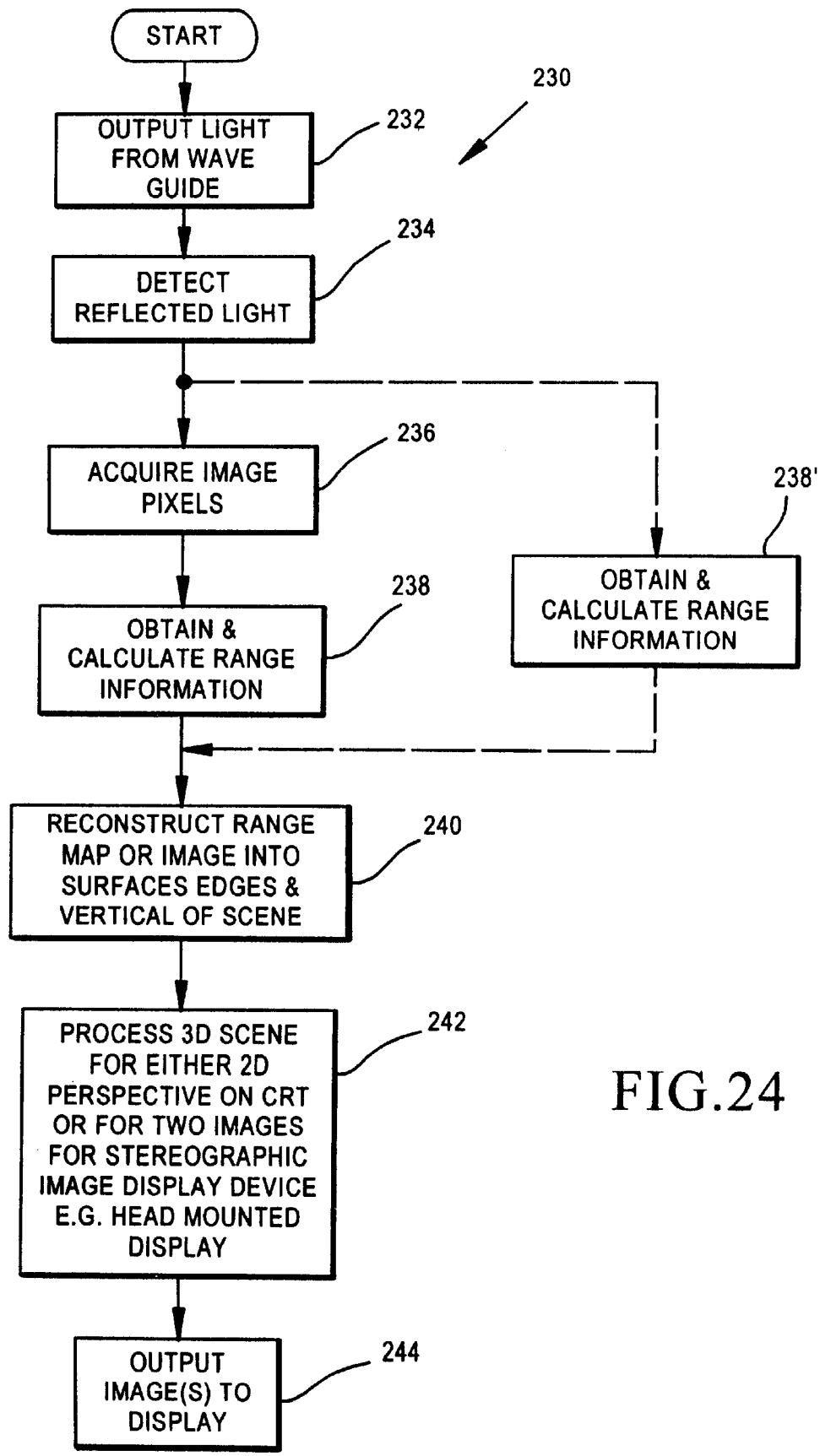
FIG. 24 is a flow chart of a method for acquiring an image with enhanced depth information according to another embodiment of this invention.

Referring to FIG. 24, a method 230 for acquiring an image including depth information is presented. At step 232, a beam of light 30/32 is output from a resonant fiber waveguide 36 (see FIG. 2). The waveguide 36 scans the output beam along a scan path. The scan lens 39 focuses the beam onto the an object's surface (i.e., target). At a given time the beam is focused to impinge on a spot of the target, the spot being an illuminated spot, the illuminated spot varying with time as the beam is scanned along the target surface.

At step 234, returning light from the target surface is detected by at least one detector 50. At step 236, a plurality of pixels for an image are acquired from the returning light detected by the detector either at the distal tip or after a light-collecting optical fiber. At step 238, range information also is acquired from the returning light using any of the range finding methods described above (e.g., phase shift, time of flight, frequency, interferometry), subsequent to, or preferably in parallel to step 236.

At step 240, the range information is used to map surface, edges and vertices of the scene imaged (e.g., topography of target). At step 242, the three dimensional image data derived in step 240 is processed to achieve pixel data for display on a display screen or other output device, such as a stereographic head mounted display. For example, where a stereographic head mounted display is used, a viewer's binocular disparity is calculated to derive a pair of stereographic images. At step 244, pixel data of the output images is output to the display.

In an alternative embodiment, a second detector is used to detect the range information from the returning light using any of the range finding methods described above. In still another embodiment, the output beam includes a beam of light for imaging the object being scanned. Such output beam is either monochromatic or a color beam of visible light. In addition, the output beam also includes a coincident beam for range finding. The coincident beam is either visible light or non-visible light.

Applications

A. Endoscope/Boroscope/Catheter

Small overall diameter, best mode is ≦3 mm,

Extremely flexible shaft, containing a single optical fiber,

High resolution, theoretical limit is estimated to be 5 μm,

Very wide Field of View (FOV) is achieved, (beyond the standard 45°, up to approximately 180 degrees).

Red (R), Green (G), and Blue (B) full color detection,

Stereo image detection accomplished in either two ways:
 matched pairs of stereoscopic R, G, B light detectors helping to enhance the topographical contrast feature inherent in scanned illumination systems, quasi-stereo.
 dual image generators, diameter ≦6 mm in best mode, allowing true-stereo.

Video rates of image display (30–60 Hz refresh rate is standard),

Low cost, potentially disposable, sterilizable,

Low power, resonant scanner operation,

Simple design of few moving parts,

Can be applied to high power laser, visible, UV or IR illumination, for such medical procedures as photodynamic therapy, laser-induced fluorescence, laser surgery, IR imaging in blood, etc., Can be applied to high power, short-pulsed UV, visible, or IR illumination for such medical applications as measuring distances between the scope and tissue (range finding and true 3D imaging), multi-photon fluorescence imaging, and fluorescent lifetime imaging, Small size and flexibility allows the image generator to be retrofitted to existing endoscopes (cannulas), flexible sheaths, or attached to surgical or diagnostic tools, Flexibility in bending as well as rotation with single fiber axially symmetric optical coupling The acquired photoelectric signal is directly compatible with video signal inputs of RGB video monitors, especially having multi-synch capabilities, The backscattered light is guided by optical fibers directly from the distal end to the viewer's eye at the proximal end eliminating the need for photodetectors at the distal end. In addition to a standard video display monitor, the image is displayed in one embodiment by a retinal scanning device without the need for electronic signal conversion B. Other Applications: Remote Optical Sensing, Robotic eyes placed at the fingertips of the robotic hands or graspers, Long-Term Process Monitoring; Eye Tracker, Bar Code Reader, Range Finder, microlithography, visual displays, optical inspection, and laser surgery.

Meritorious and Advantageous Effects

An advantage of the invention is that flexibility of the fiber, a wide field of view and high resolution are achieved even for small, thin scopes due to the method in which pixels are obtained, the presence of the lenses and the manner of driving the fiber. Because pixels are measured in time series and not in a 2-D pixel array, it is not mandatory to have small photon detectors. The size of the detector is not critical as in the prior scopes where many small detectors spanned a large area. Therefore, a scope of this invention can be made smaller than existing scopes while using fewer photon detectors that are larger than the pixel detectors of standard scopes.

According to another advantage of the invention, a high resolution, high field of view, scanning, flexible fiber device is achieved. In particular by locating the fiber resonant node at the distal end of the resonating waveguide portion of the fiber, a wide scanning angle is achieved in a relatively small fiber movement area. This allows for both high resolution and a wide field of view. By using a small spot size and by time capturing the detected light in correlation to the illumination light, a high pixel resolution is achieved. With the small size and low power consumption, a low cost, disposable scanning device is achieved.

Although a preferred embodiment of the invention has been illustrated and described, various alternatives, modifications and equivalents may be used. For example, in some embodiments, a sensor is mounted at the tip of the fiberoptic scanner to detect the fiber position and aid in controlling the scan pattern using an electromagnetic, electrostatic. electromechanical, optical, or sonic control.

In alternative embodiments, a variable or non-rectilinear scan pattern is implemented, such as an elliptical pattern with varying radii and centroid location. For example, such customized scan patterns such as rotating linear or radial patterns are desirable for single actuator, small sized eye-tracking and bar-code reading implementations.

Alternative methods for implementing a second slower, orthogonal scanning axis include moving a mirror, lens(es), gratings, or combinations of the same. Such optical components are located between the fast scanning resonant fiber and the target object.

In some embodiments the tip of the fiber 26 is tapered (i) to reduce the mass of the fiber tip for increased scan amplitude, (ii) to reduce physical range of scan motion, and/or (iii) to reduce effective point source size of light emission.

In some embodiments polarization maintaining illumination components and polarization filters are included to reject backscattered light that has undergone multiple scattering and color shifting. In some embodiments the wave guide is a cantilever having a light source at the distal end of the waveguide where light is emitted.

Although a scanning optical fiber waveguide is described, in an alternative embodiment of the method of depth enhancement and the method of range finding, a deflecting mirror or a cantilever assembly are used to scan the output beam onto the target object.

Although in the preferred embodiment visible light is emitted and detected, in alternative embodiments the emitted and detected light is ultraviolet light, infrared. In some embodiment sensors are included which provide feedback to a drive system controller which in response adjusts the deflection of the cantilever. As a result, the deflection of the cantilever is adjusted and controlled.

Therefore, the foregoing description should not be taken as limiting the scope of the inventions which are defined by the appended claims.

What is claimed is:

1. A method for generating an image of a target surface, comprising the steps of:
    outputting a beam of light along a scan path relative to an optical axis;
    focusing the beam onto a target surface being scanned, wherein at a given time the beam is focused to impinge on a spot of the target, the spot being an illuminated spot, the illuminated spot varying with time as the beam is scanned onto the target surface;
    detecting light returning from the target surface responsive to the output beam of light with a plurality of detectors, each one of the plurality of detectors having a respective location relative to the optical axis, wherein the returning light is detected concurrently at the plurality of detectors;
    acquiring a plurality of concurrent images with the plurality of detectors;
    wherein the plurality of concurrent images have a common apparent viewpoint based upon a common light beam being used to generate the returning light, the common light beam being said output beam of light;
    wherein each one image of the plurality of concurrent images has a differing apparent lighting direction, the apparent lighting direction for a given one image of the plurality of images being based upon the respective location of a corresponding one or more detectors of the plurality of detectors used to acquire said given one image; and
    processing the plurality of concurrent images to derive an output image of the target surface, including relative depth information based upon the differing apparent lighting direction from each one image of the plurality of concurrent images.

2. The method of claim 1, wherein the step of detecting comprises detecting light returning from an area of the target surface which is greater than an area defined the illuminated spot.

3. The method of claim 1, in which the step of processing comprises generating an orientation map of target surface normals based upon the first image and second image.

4. The method of claim 3, in which the step of processing further comprises the step of creating an orientation histogram from the orientation map and comparing the orientation histogram to one or more prototype orientation histograms to classify the target surface.

5. The method of claim 3, in which the step of processing further comprises the step of creating a depth map from the orientation map.

6. The method of claim 3, in which the step of processing further comprises the step of creating a 3-dimensional mesh from the depth map.

7. The method of claim 6, in which the step of processing comprises rendering the 3-dimensional mesh with virtual lighting and viewpoint to enhance either one or both of depth perception and surface topography.

8. The method of claim 6, in which the step of processing comprises computing two stereographic images from the 3-dimensional mesh in which a viewer's binocular disparity is calculated.

9. The method of claim 1, in which the step of processing comprises rendering the output image to exhibit enhanced surface topography in relation to each one of the plurality of concurrent images.

10. The method of claim 1, in which the step of processing comprises rendering the output image to exhibit enhanced lighting perspective relative to each one of the plurality of concurrent images.

11. The method of claim 1, in which the step of processing comprises rendering two stereographic images in which a viewer's binocular disparity is calculated, the two stereographic images being output images to a viewer's eyes.

12. The method of claim 1, wherein the output beam of light comprises visible light and ultraviolet light, wherein the first detector detects returning visible light and the second detector detects returning ultraviolet light.

13. The method of claim 1, wherein the output beam of light comprises visible light and infrared light, wherein a first detector of the plurality of detectors detects returning visible light and a second detector of the plurality of detectors detects returning infrared light.

14. The method of claim 1, in which the beam of light is an output beam of light emitting from a resonant waveguide, and further comprising, prior to the step of outputting the steps of:
    generating a first beam of light of a first color, a second beam of light of a second color and a third beam of light of a third color; and
    combining the first beam, the second beam and the third beam before entering the resonant waveguide, the combined first beam, second beam and third beam forming the output beam.

15. The method of claim 1, in which the output beam of light is a sequence of light pulses, and wherein the step of detecting is synchronized with the sequence of light pulses, the detected returning light at said given time corresponding to a given light pulse and said acquired pixel.

16. The method of claim 1 wherein the step of detecting returning light comprises detecting reflected light.

17. The method of claim 1 wherein the step of detecting returning light comprises detecting fluorescent light emitted from the target surface responsive to the output beam.

18. The method of claim 1 wherein the step of detecting returning light comprises detecting phosphorescent light emitted from the target surface responsive to the output beam.

19. A system for acquiring an image of a target surface, comprising:
   a light source which emits light;
   an actuator which deflects the emitted light along a scan path relative to an optical axis;
   a plurality of photon detectors for detecting light returning from the target surface responsive to the emmitted light, each one of the plurality of photon detectors having a distinct location relative to the optical axis, wherein a plurality of concurrent images are acquired with the plurality of detectors, the plurality of concurrent images have a common apparent viewpoint based upon a common light beam being used to generate the returning light, the common light beam being said output beam of light, each one image of the plurality of concurrent images having a differing apparent lighting direction, the apparent lighting direction for a given one image of the plurality of images being based upon the respective location of a corresponding one or more detectors of the plurality of detectors used to acquire said given one image; and
   a processor which processing the plurality of concurrent images to derive an output image of the target surface, including depth information based upon the differing apparent lighting direction from each one image of the plurality of concurrent images.

20. The system of claim 19, further comprising:
   a flexible, optical waveguide which receives the emitted light and directs the light toward a target surface, wherein at a given time the light impinges on a spot of the target surface, the spot being an illuminated spot; and
   wherein the actuator deflects the waveguide into a resonant motion, the directed light tracing a scan path along the target surface.

21. The system of claim 19, further comprising:
   a mirror which receives the emitted light and directs the light toward a target surface, wherein at a given time the light impinges on a spot of the target surface, the spot being an illuminated spot; and
   wherein the actuator deflects the mirror, the directed light tracing a scan path along the target surface.

22. The system of claim 19, further comprising:
   a cantilever assembly having a light source at a distal cantilever tip that emits light out along an axis of the cantilever toward a target surface, wherein at a given time the light impinges on a spot of the target surface, the spot being an illuminated spot; and
   wherein the actuator deflects the cantilever assembly, the directed light tracing a scan path along the target surface.

23. The system of claim 19, in which each one of the plurality of detectors has an active viewing area of the target surface which exceeds size of the illuminated spot; and further comprising a correlator which correlates sampling time of the detector with the light as the light traces a scan path, wherein pixels are acquired of an image of a portion of the target surface, wherein resolution of each one pixel of the acquired pixels corresponds to the size of the illuminated spot; and wherein a first one of the concurrent images is acquired from the first set of detectors.

24. The system of claim 19, wherein the output beam of light is a combination of a first color light beam, a second color light beam and a third color light beam, and wherein the output image is a color image;
   wherein the plurality of detectors comprises a first set of detectors, the first set of detectors including a first color first detector for detecting returning light of the first color light beam, a second color first detector for detecting returning light of the second color light beam, and a third color first detector for detecting returning light of the third color light beam, and wherein a first one of the plurality of concurrent images is acquired from the first set of detectors.

25. The system of claim 24, wherein the plurality of detectors comprises a second set of detectors, the second set of detectors including a first color second detector for detecting returning light of the first color light beam, a second color second detector for detecting returning light of the second color light beam, and a third color second detector for detecting returning light of the third color light beam, and wherein a second one of the plurality of concurrent images is acquired from the second set of detectors.

26. The system of claim 24, wherein the plurality of detectors further comprises a second detector, the second detector being a multiwavelength detector for detecting brightness of the returning light from the first color light beam, second color light beam and third color light beam, wherein a second one of the plurality of concurrent images is acquired from the second detector.

27. The system of claim 26, wherein the plurality of detectors further comprises a third detector, and wherein a third one of the plurality of concurrent images is acquired from the third detector.

28. The system of claim 19, wherein the plurality of detectors comprises a first detector and a second detector, the first detector used for acquiring a first one of the concurrent images, the second detector used for acquiring a second one of the plurality of concurrent images.

29. The system of claim 28, wherein the plurality of detectors further comprises a third detector for acquiring a third one of the plurality of concurrent images.

30. The system of claim 19, wherein the processor generates an orientation map of target surface normals based upon the plurality of concurrent images.

31. The system of claim 30, wherein the processor creates an orientation histogram from the orientation map and compares the orientation histogram to one or more prototype orientation histograms to classify the target surface.

32. The system of claim 30, wherein the processor creates a depth map from the orientation map.

33. The system of claim 32, wherein the processor creates a 3-dimensional mesh from the depth map.

34. The system of claim 33, wherein the processor renders the 3-dimensional mesh with virtual lighting and viewpoint to enhance either one or both of depth perception and surface topography.

35. The system of claim 34, wherein the processor computes two stereographic images from the 3-dimensional mesh in which a viewer's binocular disparity is calculated.

* * * * *